United States Patent
Monkowski et al.

(10) Patent No.: US 12,372,771 B2
(45) Date of Patent: Jul. 29, 2025

(54) SYSTEMS AND METHODS FOR ACTIVELY MITIGATING VIBRATIONS

(71) Applicant: 10x Genomics, Inc., Pleasanton, CA (US)

(72) Inventors: Adam Joseph Monkowski, Pleasanton, CA (US); Elijah Roberts, Pleasanton, CA (US); Benjamin Pruitt, Cambridge, MA (US)

(73) Assignee: 10x Genomics, Inc., Pleasanton, CA (US)

( * ) Notice: Subject to any disclaimer, the term of this patent is extended or adjusted under 35 U.S.C. 154(b) by 71 days.

(21) Appl. No.: 18/508,976

(22) Filed: Nov. 14, 2023

(65) Prior Publication Data
US 2024/0168273 A1 May 23, 2024

Related U.S. Application Data

(60) Provisional application No. 63/426,689, filed on Nov. 18, 2022.

(51) Int. Cl.
*G02B 21/36* (2006.01)
*G02B 21/16* (2006.01)
(Continued)

(52) U.S. Cl.
CPC .......... *G02B 21/367* (2013.01); *G02B 21/16* (2013.01); *G02B 21/26* (2013.01); *G02B 21/361* (2013.01);
(Continued)

(58) Field of Classification Search
CPC ...... G02B 21/367; G02B 21/16; G02B 21/26; G02B 21/361; H04N 23/683; H04N 23/6812; H04N 23/55; A61B 90/20
(Continued)

(56) References Cited

U.S. PATENT DOCUMENTS

| 5,599,675 A | 2/1997 | Brenner |
| 5,750,341 A | 5/1998 | Macevicz |

(Continued)

FOREIGN PATENT DOCUMENTS

| WO | WO 2018/026873 | 2/2018 |
| WO | WO 2021/138676 | 7/2021 |

(Continued)

OTHER PUBLICATIONS

Chen et al., "Spatially Resolved, Highly Multiplexed RNA Profiling In Single Cells", *Science*, 348(6233): aaa6090, 2015.
(Continued)

*Primary Examiner* — Allen C Wong
(74) *Attorney, Agent, or Firm* — Stephen J. Kenny; Foley Hoag LLP

(57) ABSTRACT

Various embodiments of the present disclosure disclose methods and systems for actively monitoring an opto-fluidic instrument for vibrational disturbances and correcting images obtained during the detected disturbances. In various embodiments, an optical imaging system may acquire Z-stack images of samples supported by an XY-stage. Vibrations can cause individual stacks to be sheared, i.e., to not be co-located with respect to neighboring Z-stacks. In various embodiments, an offset between the measured positions and the expected positions of the sheared stacks may be computed, and a determination as to whether to correct or reacquire the Z-stack images may be made based at least in part on the computed offset.

20 Claims, 11 Drawing Sheets

(51) Int. Cl.
- *G02B 21/26* (2006.01)
- *H04N 23/55* (2023.01)
- *H04N 23/68* (2023.01)
- *A61B 90/20* (2016.01)

(52) U.S. Cl.
CPC ......... *H04N 23/55* (2023.01); *H04N 23/6812* (2023.01); *H04N 23/683* (2023.01); *A61B 90/20* (2016.02)

(58) Field of Classification Search
USPC .......................................................... 348/79
See application file for complete search history.

(56) References Cited

U.S. PATENT DOCUMENTS

| | | |
|---|---|---|
| 6,172,218 B1 | 1/2001 | Brenner |
| 6,306,597 B1 | 10/2001 | Macevicz |
| 6,969,488 B2 | 11/2005 | Bridgham et al. |
| 7,057,026 B2 | 6/2006 | Barnes et al. |
| 7,632,641 B2 | 12/2009 | Dirks et al. |
| 7,709,198 B2 | 5/2010 | Luo et al. |
| 8,551,710 B2 | 10/2013 | Bernitz et al. |
| 8,604,182 B2 | 12/2013 | Luo et al. |
| 8,658,361 B2 | 2/2014 | Wu et al. |
| 8,951,726 B2 | 2/2015 | Luo et al. |
| 9,217,178 B2 | 12/2015 | Fedurco et al. |
| 10,138,509 B2 | 11/2018 | Church et al. |
| 10,179,932 B2 | 1/2019 | Church et al. |
| 10,450,599 B2 | 10/2019 | Pierce et al. |
| 10,457,980 B2 | 10/2019 | Cai et al. |
| 10,494,662 B2 | 12/2019 | Church et al. |
| 10,550,429 B2 | 2/2020 | Harada et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Ost et al. |
| 2007/0166705 A1 | 7/2007 | Milton et al. |
| 2009/0118128 A1 | 5/2009 | Liu et al. |
| 2011/0059865 A1 | 3/2011 | Smith et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2014/0043461 A1* | 2/2014 | Otsuka ................. G06V 20/695 382/133 |
| 2014/0160559 A1 | 6/2014 | Mermelstein et al. |
| 2016/0024555 A1 | 1/2016 | Church et al. |
| 2016/0108458 A1 | 4/2016 | Frei et al. |
| 2016/0369329 A1 | 12/2016 | Cai et al. |
| 2017/0009278 A1 | 1/2017 | Söderberg et al. |
| 2017/0220733 A1 | 8/2017 | Zhuang et al. |
| 2018/0356621 A1 | 12/2018 | Ward et al. |
| 2019/0055594 A1 | 2/2019 | Samusik et al. |
| 2019/0106733 A1 | 4/2019 | Kishi et al. |
| 2019/0161796 A1 | 5/2019 | Hauling et al. |
| 2019/0177800 A1 | 6/2019 | Boutet et al. |
| 2019/0194709 A1 | 6/2019 | Church et al. |
| 2019/0339204 A1 | 11/2019 | Singer et al. |
| 2019/0367969 A1 | 12/2019 | Belhocine et al. |
| 2020/0224243 A1 | 7/2020 | Desai et al. |
| 2020/0224244 A1 | 7/2020 | Nilsson et al. |
| 2020/0310557 A1* | 10/2020 | Parkos ................... G06F 3/038 |
| 2021/0164039 A1 | 6/2021 | Wang et al. |
| 2021/0340618 A1 | 11/2021 | Kühnemund et al. |
| 2022/0010358 A1 | 1/2022 | Kühnemund et al. |
| 2022/0043251 A1 | 2/2022 | Moore et al. |
| 2022/0064697 A1 | 3/2022 | Zhuang et al. |
| 2023/0138764 A1* | 5/2023 | Truong ................ G02B 21/361 359/374 |

FOREIGN PATENT DOCUMENTS

| | | |
|---|---|---|
| WO | WO 2021/167526 | 8/2021 |
| WO | WO 2022/046738 A1 | 3/2022 |

OTHER PUBLICATIONS

Choi et al., "Third-Generation In Situ Hybridization Chain Reaction: Multiplexed, Quantitative, Sensitive, Versatile, Robust", *Development*, 145(12): dev165753, 2018.

Eng et al., "Transcriptome-Scale Super-Resolved Imaging in Tissues By Rna SeqFISH+", *Nature*, 568(7751): 235-239, 2019.

Frei et al., "Highly Multiplexed Simultaneous Detection Of RNAs And Proteins In Single Cells", *Nat Methods*, 13(3): 269-275, 2016.

Goh et al., "Highly Specific Multiplexed RNA Imaging In Tissues With Split-FISH", *Nat Methods*, 17(7): 689-693, 2020.

Gyllborg et al., "Hybridization-Based In Situ Sequencing (HybISS) For Spatially Resolved Transcriptomics In Human And Mouse Brain Tissue", *Nucleic Acid Res*, 48(19): e112, 2020.

Lee et al., "Highly Multiplexed Subcellular RNA Sequencing In Situ", *Science*, 342(6177): 1360-1363, 2014.

Mitra et al., "Fluorescent In Situ Sequencing On Polymerase Colonies", *Anal. Biochem*, 320: 55-65, 2003.

Moffitt et al., "RNA Imaging With Multiplexed Error-Robust Fluorescence In Situ Hybridization (MERFISH)", *Methods of Enzymology*, 572: 1-49, 2016.

Nagendran et al., "Automated Cell-Type Classification In Intact Tissues By Single-Cell Molecular Profiling", *eLife*, 7: e30510, 2018.

Shendure et al., "Accurate Multiplex Polony Sequencing Of An Evolved Bacterial Genome", *Science*, 309: 1728-1732, 2005.

Tripathi et al., "Z Probe, An Efficient Tool For Characterizing Long Non-Coding RNA In FFPE Tissues", *Noncoding RNA*, 4(3): 20, 2018.

Wang et al., "Three-Dimensional Intact-Tissue Sequencing Of Single-Cell Transcriptional States", *Science*, 361(6499): 5691, 2018.

Wu et al., "RollFISH Achieves Robust Quantification Of Single-Molecule RNA Biomarkers In Paraffin-Embedded Tumor Tissue Samples", *Commun Biol*, 1, 209, 2018.

Yang et al., "Single-Cell Phenotyping Within Transparent Intact Tissue Through Whole-Body Clearing", *Cell*, 158(4): 945-958, 2014.

International Search Report and Written Opinion for Application No. PCT/US23/79639, mailed Mar. 5, 2024, 15 pages.

* cited by examiner

SYSTEMS AND METHODS FOR ACTIVELY MITIGATING VIBRATIONS

CROSS REFERENCE TO RELATED APPLICATION

This application claims priority to and the benefit of U.S. provisional patent application Ser. No. 63/426,689, filed Nov. 18, 2022, the entire content of which is incorporated herein by reference and relied upon.

FIELD OF THE DISCLOSURE

The present disclosure is directed to methods, systems, and computer program products for vibration mitigation in an instrument. In particular, the present disclosure describes methods and systems for actively monitoring an instrument having integrated optics and fluidics modules (e.g., an in situ analysis system) for vibrational disturbances and correcting images obtained during the detected disturbances.

SUMMARY

Various embodiments of the present disclosure describe a method comprising acquiring, using an optical imaging system, a first plurality of Z-stack images of a sample supported by an XY-stage. In some instances, the first plurality of Z-stack images are images of a plurality of two-dimensional (2D) slices of the sample. The method further comprises measuring, using a position sensor coupled to the XY-stage and/or the optical imaging system, a position of one of the plurality of 2D slices. In some instances, one of the first plurality of Z-stack images is an image of the one of the plurality of 2D slices. Further, the method comprises computing, using a processor coupled to the position sensor, a position offset between the measured position and an expected position, of the one of the plurality of 2D slices. In addition, the method comprises determining whether to adjust, using the processor, position information associated with the one of the first plurality of Z-stack images, or acquire, using the optical imaging system, a second plurality of Z-stack images of the sample, based at least in part on a comparison of the position offset and the threshold offset.

Some embodiments of the present disclosure describe a system comprising an XY-stage, an optical imaging system, a position sensor and a processor. In various embodiments, the XY-stage is configured to support a sample. In various embodiments, the optical imaging system is configured to acquire a first plurality of Z-stack images of the sample. In some instances, the first plurality of Z-stack images are images of a plurality of two-dimensional (2D) slices of the sample. In various embodiments, the position sensor is coupled to the XY-stage and/or the optical imaging system, and is configured to measure a position of one of the plurality of 2D slices. In some instances, one of the first plurality of Z-stack images is an image of the one of the plurality of 2D slices. In various embodiments, the processor is coupled to the position sensor and is configured to compute a position offset between the measured position and an expected position, of the one of the plurality of 2D slices. Further, the processor is configured to determine whether to adjust, using the processor, position information associated with the one of the first plurality of Z-stack images, or acquire, using the optical imaging system, a second plurality of Z-stack images of the sample, based at least in part on a comparison of the position offset and the threshold offset.

Some embodiments of the present disclosure describe a method, a system including a computing node and a computer product comprising a computer readable storage medium, the computer node and the computer readable storage medium each comprising a computer readable storage medium having program instructions embodied therewith, the program instructions executable by a processor to cause the processor to perform the method. In various embodiments, the method comprises receiving a first plurality of Z-stack images of a sample disposed on a stage. Further, for each image in the plurality of Z-stack images, the method comprises receiving one or more position measurements of the stage associated with the image; assigning the one or more position measurements to the image; determining at least one position offset between the one or more position measurements and a nominal position; and if the position offset is below a threshold offset, adjusting the one or more position measurements associated with the image, otherwise, if the position offset is above the threshold offset, providing an indication to an optical imaging system to acquire a second plurality of Z-stack images of the sample.

BRIEF DESCRIPTION OF THE DRAWINGS

For a more complete understanding of the principles disclosed herein, and the advantages thereof, reference is now made to the following descriptions taken in conjunction with the accompanying drawings, in which.

Figure 1:
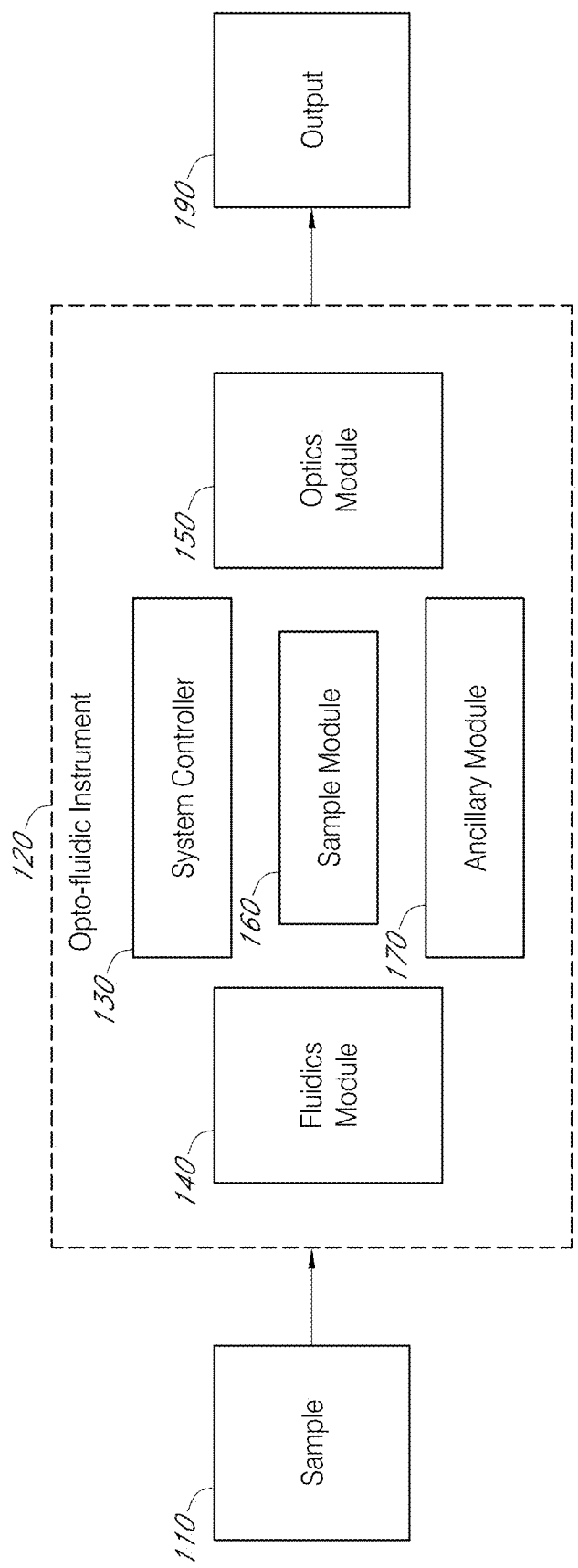
FIG. 1 is an example workflow of analysis of a biological sample (e.g. various cell, tissue, fluid, etc. sample and/or swab), using an opto-fluidic instrument analysis system, according to various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

I. Overview

Target molecules (e.g., nucleic acids, proteins, antibodies, etc.) can be detected in biological samples (e.g., one or more cells or a tissue sample) using an instrument having integrated optics and fluidics modules (an "opto-fluidic instrument" or "opto-fluidic system"). In an opto-fluidic instrument, the fluidics module is configured to deliver one or more reagents (e.g., fluorescent probes) to the biological sample and/or remove spent reagents therefrom. Additionally, the optics module is configured to illuminate the biological sample with light having one or more spectral emission curves (over a range of wavelengths) and subsequently capture one or more images of emitted light signals from the biological sample during one or more probing cycles. In various embodiments, the captured images may be processed in real time and/or at a later time to determine the presence of the one or more target molecules in the biological sample, as well as three-dimensional position information associated with each detected target molecule. Additionally, the opto-fluidics instrument includes a sample module configured to receive (and, optionally, secure) one or more biological samples. In some instances, the sample module includes an X-Y stage configured to move the biological sample along an X-Y plane (e.g., perpendicular to an objective lens of the optics module).

In various embodiments, the opto-fluidic instrument is configured to analyze one or more target molecules in their naturally occurring place (i.e., in situ) within the biological sample. For example, an opto-fluidic instrument may be an in situ analysis system used to analyze a biological sample and detect target molecules including but not limited to DNA, RNA, proteins, antibodies, and/or the like.

A sample disclosed herein can be or be derived from any biological sample. Biological samples may be obtained from any suitable source using any of a variety of techniques including, but not limited to, biopsy, surgery, and laser capture microscopy (LCM), and generally includes cells, tissues, and/or other biological material from the subject. A biological sample can be obtained from a prokaryote such as a bacterium, an archaea, a virus, or a viroid. A biological sample can also be obtained from eukaryotic mammalian and eukaryotic non-mammalian organisms (e.g., a plant, a fungus, an insect, an arachnid, a nematoda, reptile, or an amphibian A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic subjects, subjects that have or are suspected of having a disease (e.g., an individual with a disease such as cancer) or a pre-disposition to a disease, and/or subjects in need of therapy or suspected of needing therapy.

The biological sample can include any number of macromolecules, for example, cellular macromolecules and organelles (e.g., mitochondria and nuclei). The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

In some embodiments, the biological sample may comprise cells or a tissue sample which are deposited on a substrate. As described herein, a substrate can be any support that is insoluble in aqueous liquid and allows for positioning of biological samples, analytes, features, and/or reagents on the support. In some embodiments, a biological sample is attached to a substrate. In some embodiments, the substrate is optically transparent to facilitate analysis on the opto-fluidic instruments disclosed herein. For example, in some instances, the substrate is a glass substrate (e.g., a microscopy slide, cover slip, or other glass substrate). Attachment of the biological sample can be irreversible or reversible, depending upon the nature of the sample and subsequent steps in the analytical method. In certain embodiments, the sample can be attached to the substrate reversibly by applying a suitable polymer coating to the substrate and contacting the sample to the polymer coating. The sample can then be detached from the substrate, e.g., using an organic solvent that at least partially dissolves the polymer coating. Hydrogels are examples of polymers that are suitable for this purpose. In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay using the opto-fluidic instruments disclosed herein. Except where indicated otherwise, the preparative or processing steps described below can generally be combined in any manner and in any order to appropriately prepare or process a particular sample for and/or analysis.

For example, a biological sample can be harvested from a subject (e.g., via surgical biopsy, whole subject sectioning) or grown in vitro on a growth substrate or culture dish as a population of cells and prepared for analysis as a tissue slice or tissue section (e.g., a fresh frozen, fixed frozen, or formalin fixed paraffin embedded (FFPE) tissue section). The thickness of a tissue section typically depends on the method used to prepare the section and the physical characteristics of the tissue, and therefore sections having a wide variety of different thicknesses can be prepared and used.

In some instances, the biological sample is fixed in any of a variety of suitable fixatives to preserve the biological structure of the sample prior to analysis. Exemplary fixatives include formalin, formaldehyde, ethanol, methanol, acetone, paraformaldehyde (PFA)-Triton, and combinations thereof.

In some embodiments, a biological sample can be permeabilized to facilitate transfer of analytes out of the sample, and/or to facilitate transfer of species (such as probes or probes sets) into the sample. In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases).

In some embodiments, the biological sample is embedded in a polymer and/or crosslinked matrix (e.g., a hydrogel matrix). Embedding the sample in this manner typically involves contacting the biological sample with a hydrogel such that the biological sample becomes surrounded by the hydrogel. For example, the sample (e.g., a tissue section on a substrate, such as a glass substrate) can be embedded by contacting the sample with a suitable polymer material and activating the polymer material to form a hydrogel. In some embodiments, the hydrogel is formed such that the hydrogel is internalized within the biological sample. In some embodiments, the biological sample (including biological analytes) is immobilized in the hydrogel via cross-linking of the polymer material that forms the hydrogel. Cross-linking can be performed chemically and/or photochemically, or alternatively by any other suitable hydrogel-formation method. In some instances, biological molecules (or derivatives thereof) are cross-linked or otherwise covalently attached to the hydrogel. For example, in some embodiments, nucleic acid molecules (or derivatives thereof, such as an amplification product or probe(s) bound to cellular nucleic acid molecule) in a tissue sample are cross-linked or otherwise covalently attached to the hydrogel.

Hydrogels embedded within biological samples can be cleared using any suitable method. For example, electrophoretic tissue clearing methods or surfactant-based (e.g., sodium dodecyl sulfate (SDS)) clearing methods can be used to remove biological macromolecules from the hydrogel-embedded sample.

Tissue clearing is a process of optically resolving a sample or complex biological material, such as whole organs, large tissue, and cellular models, with minimal changes to morphology and without compromising the ability for immunolabeling or fluorescence imaging detection. In various embodiments, refractive index matching is used for obtaining fluorescence images. Mismatching among mediums can cause loss of imaging resolution, as light may also travel through the sample itself, a mounting media, glass coverslip, oil, and/or a microscope objective. In various embodiments, the amount of variable scattering of light from cellular membranes, lipids, and/or molecules of the specimen is reduced (e.g., minimized) using the various methods described herein. Heterogeneity of scattering among the cellular components may lead to an increase in opaqueness of an image. In various embodiments, a denser makeup of lipids, trafficking organelles, and other subcellular molecules may increase lateral, or non-forward, light scattered. In various embodiments, non-forward light scattering in situ may not pass through the specimen, as it is exacerbated by the continuous, pinball like, interactions of scattered light with neighboring molecules. In various embodiments, through the multiplicity of scattering, refraction, and absorbance the energy of light may be reduced or ultimately lost, leading to a distorted and white, non-translucent image. In various embodiments, a clearing reagent and mountant optically clears the sample by matching the refractive index to minimizing the light scattering through the specimen and to the microscope objective.

In various embodiments, optical clearing may be performed via various different approaches, primarily being divided into chemical and matrix-based approaches. In various embodiments, chemical approaches include aqueous-based or solvent-based approaches to achieve a highly resolved 3D image for immunolabeling, immuno-cytochemistry, immuno-histochemistry, and/or immunofluorescence. In various embodiments, aqueous-based clearing approaches are generally used to avoid dehydration and toxicity, which can destroy the integrity of a sample.

In various embodiments, passive clarity technique (PACT) is a passive tissue clearing and immunolabeling protocol. In various embodiments, PACT is used for intact thick organs. In various embodiments, RIMS includes a protocol for passive tissue clearing and immunostaining of intact organs that is compatible for long-term storage and has imaging media that preserves fluorescent markers over months.

In various embodiments, refractive index matching solutions (RIMS) may be produced with sugar or glycerol for simple, passive immersion. This may be used with thinner or smaller samples, as they are easier to clear and can maintain fluorescent protein emission. In various embodiments, such immersion techniques may achieve less than 1.5 refractive index and can take days to achieve clearing, resulting in reduced image quality when compared to solvent approaches, due to refractive index mismatching between the cleared sample, the glass coverslip, and immersion oil (glass and oil have an RI of 1.51). As sugar or glycerol solutions may take extended periods for clearing, a sample can experience considerable shrinkage while losing lipid content. In various embodiments, commercially available solutions control morphological alterations and loss of lipid content while achieving a higher refractive index of 1.52. In various embodiments, considerations for clearing include sample type and thickness so that there is minimal shrinkage of the sample and preservation of lipid content and fluorescence.

In various embodiments, perfusion-assisted agent release in situ (PARS) includes a method for whole-body clearing and phenotyping compatible with endogenous fluorescence. In various embodiments, all steps for PARS, including preservation, clearing, and labeling, are performed in situ prior to tissue extraction. In various embodiments, PARS, together with RIMS, transform opaque, intact, whole-organisms into optically transparent, fluorescently labeled samples for visualization with conventional confocal microscopy and phenotypic analysis at the cellular, subcellular, and/or single-molecule transcripts level as described in Single-Cell Phenotyping within Transparent Intact Tissue through Whole-Body Clearing by Yang et al. Cell. Vol 158, Issue 4, P 945-958, Aug. 14, 2014 (accessible online at https://doi.org/10.1016/j.cell.2014.07.017).

A biological sample may comprise one or a plurality of analytes of interest. The opto-fluidic instruments disclosed herein can be used to detect and analyze a wide variety of different analytes. In some aspects, an analyte can include any biological substance, structure, moiety, or component to be analyzed. For example, the analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g., an affinity binding partner) can be developed and detected (e.g., using the opto-fluidic instruments disclosed herein).

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof. The analyte may be a single molecule or a complex that contains two or more molecular subunits, e.g., including but not limited to complexes between proteins or peptides and nucleic acid molecules such as DNA or RNA, e.g., interactions between proteins and nucleic acids, e.g., regulatory factors, such as transcription factors, and DNA or RNA.

In some embodiments, the opto-fluidic instruments described herein can be utilized for the in situ detection and analysis of cellular analytes, (such as nucleic acid sequences), such as fluorescent in situ hybridization (FISH)-based methods, in situ transcriptomic analysis, or in situ sequencing, for example from intact tissues or samples in which the spatial information has been preserved. In some aspects, the embodiments can be applied in an imaging or detection method for multiplexed nucleic acid analysis. In some aspects, the provided opto-fluidic instruments can be used to detect a signal associated with a detectable label of a nucleic acid probe that is hybridized to a target sequence of a target nucleic acid in a biological sample.

Disclosed herein, in some aspects, are labelling agents (e.g., nucleic acid probes and/or probe sets) that are introduced into a cell or used to otherwise detect an analyte in a biological sample such as a tissue sample. The labelling agents include nucleic acid-based probes (e.g., the primary probes disclosed herein and/or any detectable probe disclosed herein) and may comprise any of a variety of entities that can hybridize to a nucleic acid, typically by Watson-Crick base pairing, such as DNA, RNA, LNA, PNA, etc. The nucleic acid probes may comprise a hybridization region that is able to directly or indirectly bind to at least a portion of a target sequence in a target nucleic acid. The nucleic acid probe may be able to bind to a specific target nucleic acid (e.g., an mRNA, or other nucleic acids disclosed herein).

Specific probe designs can vary depending on the application and any suitable probe or probe set may be utilized and detected using the opto-fluidic instruments described herein. In some aspects, the probes or probe sets described herein, or intermediate probes (e.g., a secondary probe, and/or a higher order probe) can be selected from the group consisting of a circular probe, a circularizable probe, and a linear probe. In some embodiments, a circular probe is pre-circularized prior to hybridization to a target nucleic acid and/or one or more other probes. In some embodiments, a circularizable probe is circularized (e.g., by ligation) upon hybridization to a target nucleic acid and/or one or more other probes such as a splint. In some embodiments, a linear probe can be one that comprises a target recognition sequence and a sequence that does not hybridize to a target nucleic acid, such as a 5' overhang, a 3' overhang, and/or a linker or spacer (which may comprise a nucleic acid sequence, such a one or more barcode sequence, or a non-nucleic acid moiety). In some embodiments, the sequence (e.g., the 5' overhang, 3' overhang, and/or linker or spacer) is non-hybridizing to the target nucleic acid but may hybridize to one another and/or one or more other probes, such as detectably labeled probes.

In some embodiments, a primary probe, a secondary probe, and/or a higher order probe disclosed herein can comprise a padlock-like probe or probe set, such as one described in U.S. Pat. No. 8,551,710, US 2020/0224244, US 2019/0055594, US 2021/0164039, US 2016/0108458, or US 2020/0224243, each of which is incorporated herein by reference in its entirety. Any suitable combination of the probe designs described herein can be used.

In some embodiments, the probes or probe sets described herein (e.g., a primary probe, or a secondary probe, and/or a higher order probe disclosed herein) can comprise two or more parts. In some cases, a probe can comprise one or more features of and/or be modified based on: a split FISH probe or probe set described in WO 2021/167526A1 or Goh et al., "Highly specific multiplexed RNA imaging in tissues with split-FISH," Nat Methods 17(7):689-693 (2020), which are incorporated herein by reference in their entireties; a Z-probe or probe set, such as one described in U.S. Pat. Nos. 7,709,198 B2, 8,604,182 B2, 8,951,726 B2, 8,658,361 B2, or Tripathi et al., "Z Probe, An Efficient Tool for Characterizing Long Non-Coding RNA in FFPE Tissues," Noncoding RNA 4(3):20 (2018), which are incorporated herein by reference in their entireties; an HCR initiator or amplifier, such as one described in U.S. Pat. No. 7,632,641 B2, US 2017/0009278 A1, U.S. Pat. No. 10,450,599 B2, or Choi et al., "Third-generation in situ hybridization chain reaction: multiplexed, quantitative, sensitive, versatile, robust," Development 145(12): dev165753 (2018), which are incorporated herein by reference in their entireties; a PLAYR probe or probe set, such as one described in US 2016/0108458 A1 or Frei et al., "Highly multiplexed simultaneous detection of RNAs and proteins in single cells," Nat Methods 13(3):269-75 (2016), which are incorporated herein by reference in their entireties; a PLISH probe or probe set, such as one described in US 2020/0224243 A1 or Nagendran et al., "Automated cell-type classification in intact tissues by single-cell molecular profiling," eLife 7:e30510 (2018), which are incorporated herein by reference in their entireties; a RollFISH probe or probe set such as one described in Wu et al., "RollFISH achieves robust quantification of single-molecule RNA biomarkers in paraffin-embedded tumor tissue samples," Commun Biol 1, 209 (2018), which is hereby incorporated by reference in its entirety; a MERFISH probe or probe set, such as one described in US 2022/0064697 A1 or Chen et al., "Spatially resolved, highly multiplexed RNA profiling in single cells," Science 348 (6233): aaa6090 (2015), which are incorporated herein by reference in their entireties; a primer exchange reaction (PER) probe or probe set, such as one described in US 2019/0106733 A1, which is hereby incorporated by reference in its entirety.

In some instances, probes and/or probe sets are directly labeled with one or more detectable labels (e.g., an optically detectable label, such as a florescent moiety) that are detected on the opto-fluidic instruments disclosed herein. In other instances, probes and/or probe sets comprise a target binding region and one or more nucleic acid barcode sequences that identify the analyte. In these embodiments, the barcode sequence(s) may be detected on the opto-fluidic instruments disclosed herein to identify the analyte in the sample. In some instances, a probe or probe set disclosed herein is a circularizable probe or probe set (e.g., a padlock probe or padlock-like probe) comprising a barcode region comprising one or more barcode sequences.

The probes and/or probe sets describe herein may comprise any suitable number of barcode sequences. In some embodiments, the probes or probe sets may comprise 1, 2, 3, 4, 5, 6, 7, 8, 9, 10, 11, 12, 13, 14, 15 or more, 20 or more, 30 or more, 40 or more, or 50 or more barcode sequences. As an illustrative example, a first probe may contain a first target-binding sequence, a first barcode sequence, and a second barcode sequence, while a second, different probe may contain a second target-binding sequence (that is different from the first target-binding sequence in the first probe), the same first barcode sequence as in the first probe, but a third barcode sequence instead of the second barcode sequence. Such probes may thereby be distinguished by determining the various barcode sequence combinations present or associated with a given probe at a given location in a sample.

In some embodiments, a labelling agent may include analyte binding moiety that interacts with an analyte (e.g., a protein) in the sample (e.g., a cell or tissue sample) and a reporter oligonucleotide comprising one or more barcode sequences associated with the analyte and/or analyte binding moiety. For example, a labelling agent that is specific to one type of cell feature (e.g., a first protein) may have coupled thereto a first reporter oligonucleotide, while a labelling agent that is specific to a different cell feature (e.g., a second protein) may have a different reporter oligonucleotide coupled thereto. In some embodiments, an analyte binding moiety includes, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, the nucleic acid probes, probe sets, reporter oligonucleotides, barcode sequences, etc. may be detected directly on the opto-fluidic instruments disclosed herein (e.g., primary probes comprise a detectable label, such as a florescent moiety), and/or by using secondary (or higher order) nucleic acid probes able to bind to the primary probes. In some embodiments, the nucleic acid probes (e.g., primary probes and/or secondary probes) are compatible with one or more biological and/or chemical reactions. For instance, a nucleic acid probe disclosed herein can serve as a template or primer for a polymerase (e.g., a circularized probe in a rolling circle amplification (RCA) reaction), a template or substrate for a ligase, a substrate for a click chemistry reaction, and/or a substrate for a nuclease (e.g., endonuclease or exonuclease for cleavage or digestion). In some instances, labelling agents (such as a primary probe set) are added to a biological sample (e.g., a cell or tissue sample) using the opto-fluidic instrument and subsequently detected using opto-fluidic instrument (e.g., using detectably labeled primary probes, sequential hybridization of detectable labelled oligonucleotides to primary probes, in situ sequencing (e.g., SBS, SBL, SBH), and the like). In some instances, labelling agents (such as a primary probe set) are added to a biological sample (e.g., a cell or tissue sample) outside the optofluidic instrument and the sample is loaded onto the opto-fluidic instruments disclosed herein for detection (e.g., using sequential hybridization of detectable labelled oligonucleotides, in situ sequencing (e.g., SBS, SBL, SBH), and the like).

In some embodiments, detection of the analytes, probes, probe sets, barcodes, etc. described herein can be performed in situ on the opto-fluidic instruments disclosed herein. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (e.g., nucleotide sequence) of the incorporated nucleotides or labeled primer extension products can be determined, and consequently, the nucleotide sequence of the corresponding template nucleic acid. Aspects of in situ sequencing approaches are described, for example, in Mitra et al., "Fluorescent in situ sequencing on polymerase colonies" *Anal. Biochem.* 320, 55-65 (2003), and Lee et al., "Highly Multiplexed Subcellular RNA Sequencing in Situ" *Science*, 343(6177) (2014), 1360-1363. In addition, examples of methods and systems for performing in situ sequencing are described in US 2016/0024555, US 2019/0194709, and in U.S. Pat. Nos. 10,138,509, 10,494,662 and 10,179,932.

In some embodiments, sequencing can be performed by sequencing-by-synthesis (SBS). In some embodiments, a sequencing primer is complementary to sequences at or near the target to be detected (e.g., one or more barcode(s)). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/0059865, US 2005/0100900, U.S. Pat. No. 9,217,178, US 2009/0118128, US 2012/0270305, US 2013/0260372, and US 2013/0079232.

In some embodiments, sequence analysis of nucleic acids (e.g., nucleic acids such as RCA products comprising barcode sequences) can be performed by sequential hybridization (e.g., sequencing by hybridization and/or sequential in situ fluorescence hybridization). Sequential fluorescence hybridization can involve sequential hybridization of detection probes comprising an oligonucleotide and a detectable label. In some embodiments, a method disclosed herein comprises sequential hybridization of the detectable probes disclosed herein, including detectably labeled probes (e.g., fluorophore conjugated oligonucleotides) and/or probes that are not detectably labeled per se but are capable of binding (e.g., via nucleic acid hybridization) and being detected by detectably labeled probes. Exemplary methods comprising sequential fluorescence hybridization of detectable probes are described in US 2019/0161796, US 2020/0224244, US 2022/0010358, US 2021/0340618, and WO 2021/138676, MERFISH (described for example in Moffitt, et al., "Chapter One—RNA Imaging with Multiplexed Error-Robust Fluorescence In Situ Hybridization (MERFISH)" Methods in Enzymology, 572, 1-49 (2016)), and hybridization-based in situ sequencing (HybISS) (described for example in Gyllborg et al., "Hybridization-based in situ sequencing (HybISS) for spatially resolved transcriptomics in human and mouse brain tissue," *Nucleic Acids Res* 48(19):e112 (2020)) all of which are incorporated herein by reference.

In some embodiments, sequencing can be performed using sequencing by ligation (SBL). Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al., "Accurate Multiplex Polony Sequencing of an Evolved Bacterial Genome," Science, 309: 1728-1732 (2005), and in U.S. Pat. Nos. 5,599,675; 5,750, 341; 6,969,488; 6,172,218; and 6,306,597. Exemplary techniques for in situ SBL comprise, but are not limited to, STARmap (described for example in Wang et al., "Three-dimensional intact-tissue sequencing of single-cell transcriptional states," Science, 361(6499) 5691 (2018)) and US 2021/0164039).

In some embodiments, probe barcodes (e.g., plurality of probes or probe sets comprising one or more barcode sequences) or complements or products thereof are targeted by detectably labeled detection oligonucleotides, such as fluorescently labeled oligonucleotides. In some embodiments, one or more decoding schemes (e.g., sequential rounds of fluorescent probe hybridization) are used on the opto-fluidic instruments disclosed herein to decode the signals, such as fluorescence, for sequence identification. In any of the embodiments herein, barcodes (e.g., primary and/or secondary barcode sequences) can be analyzed (e.g., detected or sequenced using the opto-fluidic instruments disclosed herein) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides or detectable probes). Exemplary decoding schemes are described in Eng et al., "Transcriptome-scale Super-Resolved Imaging in Tissues by RNA SeqFISH+," *Nature* 568(7751):235-239 (2019); Chen et al., *Science;* 348(6233): aaa6090 (2015); Gyllborg et al., *Nucleic Acids Res* 48(19):e112 (2020); U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

It is to be noted that, although the above discussion relates to an opto-fluidic instrument that can be used for in situ target molecule detection via probe hybridization, the discussion herein equally applies to any opto-fluidic instrument that employs any imaging or target molecule detection technique. That is, for example, an opto-fluidic instrument may include a fluidics module that includes fluids used for establishing the experimental conditions for the probing of target molecules in the sample. Further, such an opto-fluidic instrument may also include a sample module configured to receive the sample, and an optics module including an imaging system for illuminating (e.g., exciting one or more fluorescent probes within the sample) and/or imaging light signals received from the probed sample. The opto-fluidic instrument may also include other ancillary modules configured to facilitate the operation of the opto-fluidic instrument, such as, but not limited to, cooling systems, motion calibration systems, etc.

In various embodiments, the imaging of the sample on the sample module by the imaging system may be hampered by motion experienced by the sample module in the opto-fluidic instrument, which can be caused by internal and/or external motion sources. For example, an internal motion source can be a fluidics module that may include components such as pumps, cooling fans, etc., which may cause, when in operation, the fluidics module to vibrate. Examples of external sources of motion include pedestrians, vehicles, etc., that are in motion in the vicinity of the opto-fluidic instrument, and may trigger ambient vibrations that disturb the sample module. These motions/vibrations caused by the internal and/or external motion sources and experienced by the sample module may render sample images captured by the imaging system inaccurate. For instance, the imaging system may be configured to capture the sample images at a rate that is comparable to the frequency of the internal or external vibrations, which may result in the captured images being inaccurate representations of the sample. In turn, such inaccurate images may lead to erroneous analysis and detection of the target molecules in the sample.

Accordingly, there exists a need for methods and systems for monitoring an opto-fluidic instrument for vibrational disturbances and correcting images obtained during the detected disturbances. For example, the displacement of the sample module due to the vibrations may be less than a threshold amount. In such cases, the acquired images may be processed to correct for the effects of the vibrations. In some instances, for example when the displacement is equal to or greater than the threshold amount, a new image of the sample may be acquired, instead of or in addition to correcting the initial image for the effects of the vibrations.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

II. Example Descriptions of Terms

As used herein the specification, "a" or "an" may mean one or more. As used herein in the claim(s), when used in conjunction with the word "comprising," the words "a" or "an" may mean one or more than one. Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The use of the term "or" in the claims is used to mean "and/or" unless explicitly indicated to refer to alternatives only or the alternatives are mutually exclusive, although the disclosure supports a definition that refers to only alternatives and "and/or." For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment. As used herein "another" may mean at least a second or more.

The term "ones" means more than one.

As used herein, the term "plurality" can be 2, 3, 4, 5, 6, 7, 8, 9, 10, or more.

As used herein, the term "set of" means one or more. For example, a set of items includes one or more items.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" means item A; item A and item B; item B; item A, item B, and item C; item B and item C; or item A and C. In some cases, "at least one of item A, item B, or item C" means, but is not limited to, two of item A, one of item B, and ten of item C; four of item B and seven of item C; or some other suitable combination As used herein, the term "about" refers to include the usual error range for the respective value readily known. Reference to "about" a value or parameter herein includes (and describes) embodiments that are directed to that value or parameter per se. For example, description referring to "about X" includes description of "X". In some embodiments, "about" may refer to #15%, +10%, +5%, or +1% as understood by a person of skill in the art.

As used herein, the term "slice", "sample slice", or "two dimensional (2D) slice" of a sample refers to a 2-dimensional cross-sectional area of the sample. The slice of the sample can be perpendicular to the optical axis of the optical imaging system that is acquiring an image of the slice or 2D slice of the sample. The term "2D slice images" or "slice images" may refer to the images of the 2D slices of the sample.

As used herein, the term "3D Z-stack images" of a sample refers to a collection of (2D) images of 2D slices of a sample, where the 2D slices correspond to the focal planes of the optical imaging system that acquired the images. Successive 2D slices are separated by a prescribed distance the optical imaging system moves in the z-direction (e.g., perpendicular to the plane of the sample) between acquiring successive 2D images of successive 2D slices. Further, the term "3D imaging" of a sample may refer to acquiring 3D Z-stack images of a sample. 3D Z-stack images may also be alternatively referred to as "3D volume" (e.g., generated from Z-stack 2D images/slices.

As used herein, the term "2D slice image capture rate" refers to the frequency with which an optical imaging system acquires 2D slice images of slices of a sample. That is, the capture rate refers to the number of images of a sample captured by the optical imaging system in a second.

As used herein, the terms "co-locating" and "not co-locating" may refer to the following: a first image of a first 2D slice of a sample may have a first feature at $(x_1, y_1, z_1)$ as measured from some reference frame. A second image of a second 2D slice of the sample may have a second feature at $(x_2, y_2, z_2)$ as measured from some reference frame. The first feature and the second feature, as well as the first image and the second image, are said to be "co-located" when $x_1=x_2$ and $y_1=y_2$ (e.g., and $z_1=z_2$). The first feature and the second feature, as well as the first image and the second image, are said to "not co-locate" when $x_1 \neq x_2$ or $y_1 \neq y_2$ (for example, because a vibration caused the sample to be displaced when the first image and/or the second image are captured).

While the present teachings are described in conjunction with various embodiments, it is not intended that the present teachings be limited to such various embodiments. On the contrary, the present teachings encompass various alternatives, modifications, and equivalents, as will be appreciated by those of skill in the art.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

III. Opto-Fluidic Instruments for Analysis of Biological Samples

FIG. 1 shows an example workflow of analysis of a biological sample 110 (e.g., cell or tissue sample) using an opto-fluidic instrument 120, according to various embodiments. In various embodiments, the sample 110 can be a biological sample (e.g., a tissue) that includes molecules targeted for analysis (i.e., target molecules), such as DNA, RNA, proteins, antibodies, etc. In various embodiments, the biological sample is a fresh frozen tissue. In various embodiments, the biological sample is a formalin-fixed paraffin-embedded (FFPE) sample. For example, the sample 110 can be a sectioned tissue that is treated to access the RNA thereof for labeling with circularizable DNA probes. In various embodiments, ligation of the probes may generate a circular DNA probe which can be enzymatically amplified and bound with fluorescent oligonucleotides, to produce a sufficiently bright signal that facilitates image acquisition and has a high signal-to-noise ratio.

In various embodiments, the sample 110 may be placed in the opto-fluidic instrument 120 for analysis and detection of the target molecules in the sample 110. In various embodiments, the opto-fluidic instrument 120 is configured to facilitate the experimental conditions conducive for the detection of the target molecules. For example, the opto-fluidic instrument 120 can include a fluidics module 140, an optics module 150, a sample module 160, and at least one ancillary module 170, and these modules may be operated by a system controller 130 to create the experimental conditions for the probing of the target molecules in the sample 110 by selected probes (e.g., circularizable DNA probes), as well as to facilitate the imaging of the probed sample (e.g., by an imaging system of the optics module 150). In various embodiments, the various modules of the opto-fluidic instrument 120 may be separate components. In various embodiments, the various modules of the opto-fluid instrument may be in electrical communication with each other. In various embodiments, at least some of the modules of the opto-fluidic instrument 120 may be integrated together into a single module.

In various embodiments, the sample module 160 may be configured to receive the sample 110 in the opto-fluidic instrument 120. For instance, the sample module 160 may include a sample interface module (SIM) that is configured to receive a sample device (e.g., cassette) in which a substrate (having the sample 110 positioned thereon) can be secured. In various embodiments, the substrate is a glass slide. That is, the sample 110 may be placed in the opto-fluidic instrument 120 by securing the substrate having the sample 110 (e.g., the sectioned tissue) within the sample device that is then inserted into the SIM of the sample module 160. In various embodiments, the SIM includes an alignment mechanism configured to secure the sample device within the SIM and align the sample device in X, Y, and Z axes within the SIM. In some embodiments, the sample module 160 may also include an X-Y stage onto which the SIM is mounted. The X-Y stage may be configured to move the SIM mounted thereon (e.g., and as such the sample device containing the sample 110 inserted therein) in perpendicular directions along a two-dimensional (2D) plane of the opto-fluidic instrument 120. Additional discussion related to the SIM can be found in U.S. Provisional application Ser. No. 18/328,200, filed Jun. 3, 2022, titled "Methods, Systems, and Devices for Sample Interface," which is incorporated herein by reference in its entirety.

The experimental conditions that are conducive for the detection of the target molecules in the sample 110 may depend on the target molecule detection technique that is employed by the opto-fluidic instrument 120. For example, in various embodiments, the opto-fluidic instrument 120 can be a system that is configured to detect molecules in the sample 110 via hybridization of probes. In such cases, the experimental conditions can include molecule hybridization conditions that result in the intensity of hybridization of the target molecule (e.g., nucleic acid) to a probe (e.g., oligonucleotide) being significantly higher when the probe sequence is complementary to the target molecule than when there is a single-base mismatch. The hybridization conditions include the preparation of the sample 110 using reagents such as washing/stripping reagents, probe reagents, etc., and such reagents may be provided by the fluidics module 140.

In various embodiments, the fluidics module 140 may include one or more components that may be used for storing the reagents, as well as for transporting said reagents to and from the sample device containing the sample 110. For example, the fluidics module 140 may include one or more reservoirs configured to store the reagents, as well as a waste container configured for collecting the reagents (e.g., and other waste) after use by the opto-fluidic instrument 120 to analyze and detect the molecules of the sample 110. In various embodiments, the one or more reservoirs include one or more high use reagent reservoirs. In various embodiments, the fluidics module 140 may be configured to receive one or more low use reagent plates (e.g., a 96 deep well plate). Further, the fluidics module 140 may also include pumps, tubes, pipettes, etc., that are configured to facilitate the transport of the one or more reagents (e.g., high use reagent and/or low use reagent) to the sample device and thus contact the sample 110 with the reagent (e.g., high use reagent and/or low use reagent). For instance, the fluidics module 140 may include one or more pumps ("reagent pumps") that are configured to pump washing and/or stripping reagents (i.e., high use reagents) to the sample device for use in washing and/or stripping the sample 110. In various embodiments, the fluidics module 140 may be configured for other washing functions such as washing an objective lens of the imaging system of the optics module 150. In some embodiments, a stage (e.g., a Y-Z stage) may be configured to move the pipettes, tubes, etc., along one or more directions, to and from the sample device containing the sample 110, so that the various one or more reagents may be dispensed in the sample device, and spent reagents may be extracted from the sample device.

In various embodiments, the ancillary module 170 includes a cooling system (i.e., a heat transfer system) of the opto-fluidic instrument 120. In various embodiments, the cooling system includes a network of coolant-carrying tubes configured to transport coolants to various modules of the opto-fluidic instrument 120 for regulating the temperatures thereof. In such cases, the ancillary module 170 may include one or more heat transfer components of a heat transfer circuit. In various embodiments, the heat transfer components include one or more coolant reservoirs for storing coolants and pumps (e.g., "coolant pumps") for generating a pressure differential, thereby forcing the coolants to flow from the reservoirs to the various modules of the opto-fluidic instrument 120 via the coolant-carrying tubes. In some embodiments, the heat transfer components of the ancillary module 170 may include returning coolant reservoirs that may be configured to receive and store returning coolants, i.e., heated coolants flowing back into the returning coolant reservoirs after absorbing heat discharged by the various modules of the opto-fluidic instrument 120. In such cases, the ancillary module 170 may also include one or more cooling fans that are configured to force air (e.g., cool and/or ambient air) to the external surfaces of the returning coolant reservoirs to thereby cool the heated coolant(s) stored therein. In some embodiments, the ancillary module 170 may also include one or more cooling fans that are configured to force air directly to one or more components of the opto-fluidic instrument 120 so as to cool said one or more components. For example, the ancillary module 170 may include cooling fans that are configured to directly cool by forcing ambient air past the system controller 130 to thereby cool the same system controller 130.

As discussed above, the opto-fluidic instrument 120 may include an optics module 150 which include the various optical components of the opto-fluidic instrument 120, such as but not limited to a camera, an illumination module (e.g., including one or more LEDs and/or one or more lasers), an objective lens, and/or the like. The optics module 150 may include a fluorescence imaging system that is configured to image the fluorescence emitted by the probes (e.g., oligonucleotides) in the sample 110 after the probes are excited by light from the illumination module of the optics module 150.

In various embodiments, the system controller 130 may be configured to control the operations of the opto-fluidic instrument 120 (e.g., and the operations of one or more modules thereof). In some embodiments, the system controller 130 may take various forms, including a processor, a single computer (or computer system), or multiple computers in communication with each other. In various embodiments, the system controller 130 may be communicatively coupled with a data storage, a set of input devices, a display system, or a combination thereof. In various embodiments, some or all of these components may be considered to be part of or otherwise integrated with the system controller 130, may be separate components in communication with each other, or may be integrated together. In other embodiments, the system controller 130 can be, or may be in communication with, a cloud computing platform.

In various embodiments, the opto-fluidic instrument 120 may analyze the sample 110 and may generate the output 190 that includes indications of the presence of the target molecules in the sample 110. For instance, with respect to the example embodiment discussed above where the opto-fluidic instrument 120 employs a hybridization technique for detecting molecules, the opto-fluidic instrument 120 may perform a plurality of probing rounds on the sample 110. During the plurality of probing rounds, the sample 110 undergoes successive rounds of fluorescent probe hybridization (using two or more sets of fluorescent probes, where each set of fluorescent probes is excited by a different color channel) and is volumetrically imaged in a plurality of z-stacks to detect target molecules in the probed sample 110 in three dimensions. In such cases, the output 190 may include a plurality of light signals at specific three-dimensional locations over the plurality of probing cycles. In various embodiments, an optical signatures (e.g., a codeword) specific to each gene is determined from the detected optical signals at each three-dimensional location across the plurality of probing cycles, which allows the identification of the target molecules.

IV. Vibrational Sources Affecting Imaging of Samples in Opto-Fluidic Instruments In various embodiments, as discussed above, the optical imaging system may acquire a 3D image of the sample by capturing 2D slice images of multiple cross-sections (e.g., in the X-Y plane) of the sample that are spaced along the perpendicular z-direction. That is, the sample may be placed on the sample module of the opto-fluidic instrument and the optical imaging system may be positioned above the sample. In some instances, the sample may be larger than the field of view (FOV) of the objective lens of the optical imaging system, i.e., some sections of the sample may not be within the FOV of the objective lens. In such cases, the XY-stage on which the sample is positioned may traverse in the X- and/or Y-direction (e.g., along the plane of the sample) to allow those sections of the sample to be within the FOV of the objective lens (e.g., and as such allow the imaging of the sections).

In some instances, the optical imaging system (e.g., the objective lens) may move in the z-direction perpendicular to the plane of the sample so that the 2D focal plane of the objective lens traverses the sample in the z-direction coinciding with the 2D cross-sections or slices of the sample, and images of these 2D sample slices may be acquired by the imaging system to form a 3D stack image of the sample. In various embodiments, the optical imaging system may be a fluorescence imaging system (e.g., an epifluorescence microscopy system), and the imaging of a sample (or 2D slice thereof) may include a camera capturing fluorescence emitted by probes (e.g., oligonucleotides) in the sample after the probes are excited by light from a light source (e.g., LEDs).

In various embodiments, the movement of the sample may be facilitated by a stage supporting the sample, such as the XY-stage mentioned above, and/or one or more 1-dimensional stage (e.g., X- or Y-stage configured to move the sample in one direction (e.g., X- or Y-direction) in the sample plane), or a 3-dimensional stage (e.g., XYZ-stage). That is, in various embodiments, the sample module onto which the sample is placed may be supported by a 1-dimensional stage (e.g., an X stage, a Y stage), a 2-dimensional stage (e.g., XY-stage, two perpendicular X- and Y-stages), or a 3-dimensional stage (XYZ-stage, three mutually perpendicular X-, Y-, and Z-stages, mutually perpendicular one-dimensional stage (X-, Y-, Z-stage) and two-dimensional stages (XY-, YZ-, XZ-stages)). The X- and Y-stages may be configured to move the sample in the respective one-dimensional directions, and the XY and XYZ stages may be configured to move the sample in the xy-directions. In various embodiments, the objective lens may be supported by a Z-stage that is configured to translate the objective lens along the z-direction. The objective lens may also be supported by two- and three-dimensional stages (e.g., XYZ stage) that are capable of moving the objective lens in the z-direction.

In various embodiments, as noted above, the optical imaging system may acquire a 3D stack images of the sample by acquiring multiple images of 2D slices of the sample, where the slices are 2D cross-sections of the sample that are spaced from each other and coincide with the focal planes of the objective lens of the optical imaging system. For example, the optical imaging system may acquire 2D images of a sample slice that is within the FOV of the objective lens. If the entirety of the sample does not fall within the FOV of the objective lens, the XY-stage may move the sample in the XY-direction (e.g., x-direction, y-direction, or combination thereof) to allow the entire sample to fall within the FOV of the objective lens and be imaged. After acquiring an image of a 2D sample slice, the imaging system may repeat acquiring images of 2D sample slices as the Z-stage moves the objective lens in the Z-direction, where the sample slices that are imaged correspond to or coincide with the new focal planes of the objective lens during vertical translation of the objective lens by the Z-stage. The collection of 2D images of the sample may then make up the 3D Z-stack images of the sample (alternatively referred herein as "3D stack images" or simply as "stack images" of the sample). In various embodiments, a step distance between each 2D sample slice in the Z-stack of images is about 500 nm to about 1000 nm. In various embodiments, a step distance between each 2D sample slice in the Z-stack of images is about 500 nm to about 1500 nm. In various embodiments, a step distance between each 2D sample slice in the Z-stack of images is about 500 nm to about 2000 nm. In various embodiments, a step distance between each 2D sample slice in the Z-stack of images is about 500 nm to about 750 nm. In various embodiments, a step distance between each 2D sample slice in the Z-stack of images is about 750 nm to about 1000 nm. In various embodiments, a step distance between each 2D sample slice in the Z-stack of images is about 600 nm to about 900 nm. In various embodiments, a step distance between each 2D sample slice in the Z-stack of images is about 650 nm to about 800 nm. In various embodiments, a step distance between each 2D sample slice in the Z-stack of images is about 700 nm to about 750 nm. In various embodiments, the step distance between 2D sample slices is about 750 nm. In various embodiments, a step distance between each 2D sample slice in the Z-stack of images is equal to the z-resolution of the optical system.

In various embodiments, the imaging of the sample on the sample module by the imaging system as discussed above may be hampered or negatively affected by vibrations experienced by the stages supporting the sample module and/or the objective lens of the opto-fluidic instrument. Such vibrations can be caused by internal and/or external motion sources. An example of an internal vibration source can be a fluidics module of the opto-fluidic instrument that may include pumps, cooling fans, etc., which may cause the fluidics module to vibrate when operating. An example of an external vibration source can be pedestrians, vehicles, etc., that are in motion in the vicinity of the opto-fluidic instrument, and trigger ambient vibrations that travel to the sample module and/or the objective lens. The vibrations can be shock or bump vibrations, such as those caused by heavy walking, door slamming, etc., and/or ever-present vibrations such as those caused by the background environment of the opto-fluidic instrument (e.g., including regular pedestrian or vehicle traffic).

Figure 2A:
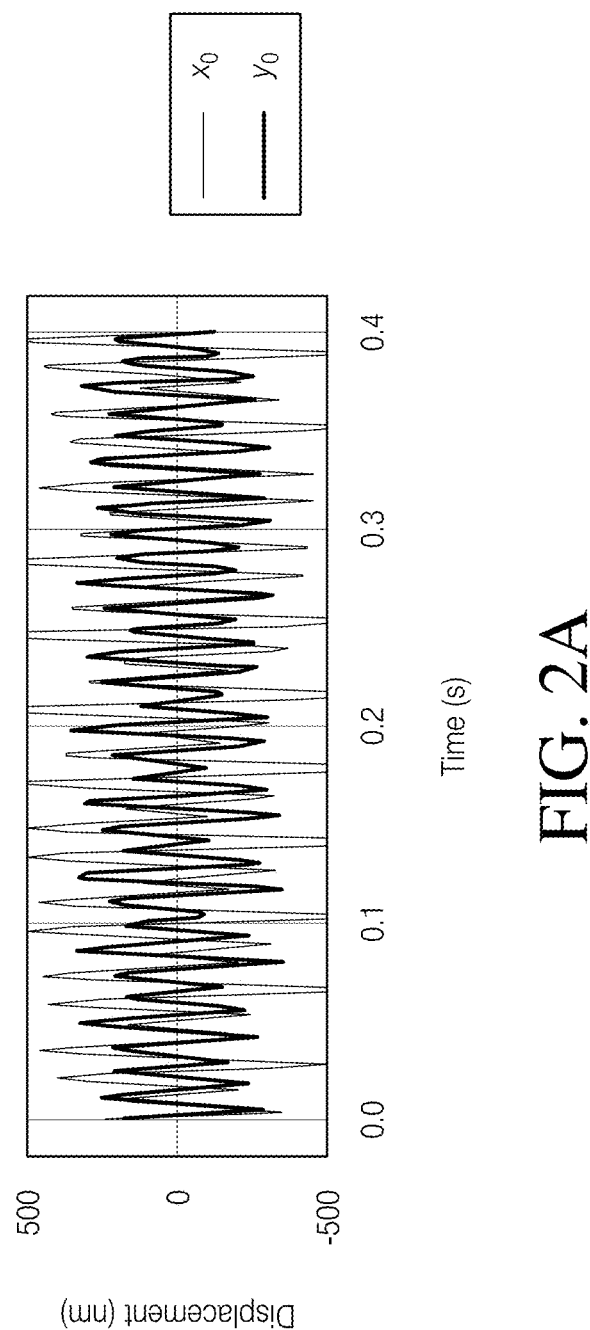
FIGS. 2A-2C illustrate vibrations experienced by a sample device of an opto-fluidic instrument as a result of the operations of internal components of the opto-fluidic instrument, according to various embodiments.
Figure 2B:
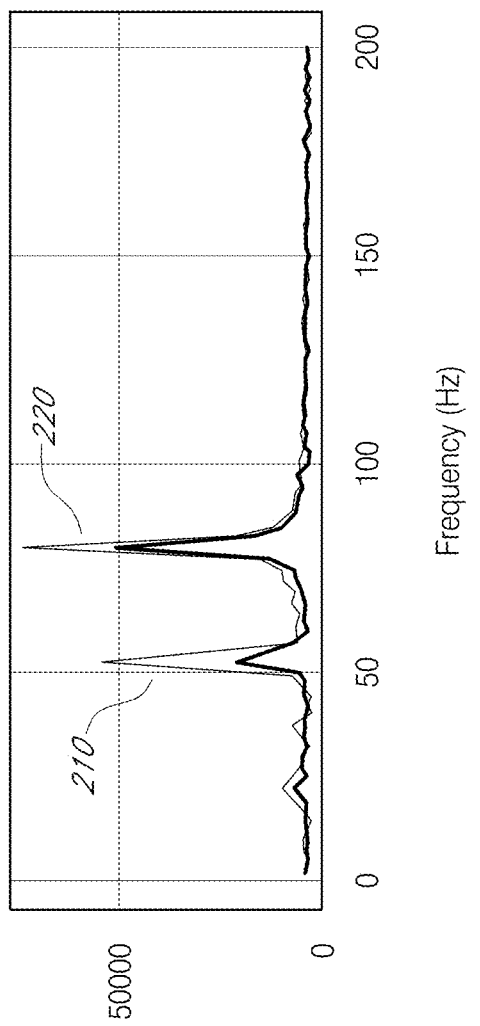
Figure 2C:
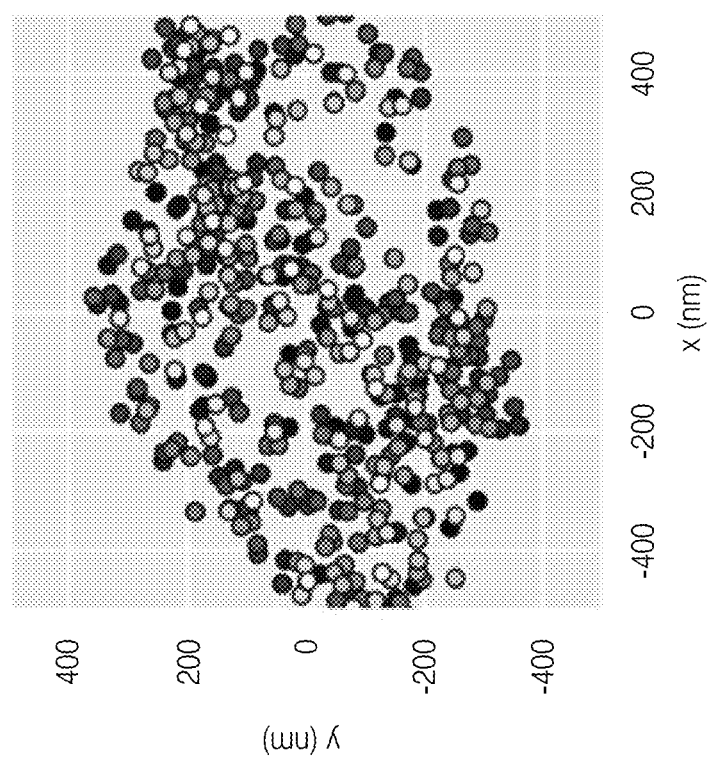

FIGS. 2A-2C illustrate vibrations experienced by a sample device of an opto-fluidic instrument as a result of the operations of internal components of the opto-fluidic instrument, according to various embodiments. In various embodiments, beads were placed on a sample device in a sample module of an opto-fluidic instrument as stand-in for samples to determine vibrations that may be experienced by the samples due to vibration sources that are internal to the opto-fluidic instrument (e.g., the opto-fluidic instrument 120, and components thereof may be the same as those discussed with reference to FIG. 1). As discussed above, the opto-fluidic instrument, such as opto-fluidic instrument 120 in FIG. 1) includes a fluidics module (such as fluidics module 140) containing movable components such as pumps, cooling fans, etc., that can be sources of vibrations. For example, the fluidics module of the opto-fluidic instrument may include reagent pumps that are used for pumping or transporting reagents between their reservoirs and sites of their use. The coolant pump may be used to pump reagents to the sample device for washing, stripping, hybridizing, etc., the sample, to the optics module of the opto-fluidic instrument for washing the objective lens, etc.). As another example, the fluidics module may include coolant pumps that may be used to pump coolants between coolant reservoirs of the opto-fluidic instrument and the various modules (e.g., optics module, fluids module) that the coolant is used for regulating the temperatures thereof. Further, the fluidics module may include fans that can be used to force ambient or cool air into the coolant reservoirs, the system controller (e.g., electronic components, etc.) of the opto-fluidic instrument 120 to cool the same.

FIGS. 2A-2C illustrate vibrations experienced by the sample device of an opto-fluidic instrument as a result of the operations of a coolant pump and cooling fans in a fluidics module of the opto-fluidic instrument, according to various embodiments. In particular, FIG. 2A shows the 2D displacement of a bead over the surface of the sample device over a time period that the coolant pump and cooling fans are in operation, which is further illustrated by a dot plot of x and y displacements of the beads shown in FIG. 2C. In the example embodiments of FIGS. 2A-2C, the bead displacements have an amplitude of about +500 nm in one direction (labeled "X-direction") and about +400 nm in the perpendicular direction ("Y-direction"). In some instances, the vibrations (e.g., amplitudes and frequencies) that are experienced by the sample device and are sources of the bead displacements shown in FIGS. 2A and 2C, can be measured by an accelerometer or a position sensor that is coupled to the XY-stage supporting the sample device. FIG. 2B shows the amplitudes and frequencies of the vibrations occurring during the same time period as that shown in FIG. 2A, illustrating that the vibrations are mainly due to two frequency modes 210, 220 corresponding respectively to the vibrational frequencies of the cooling fans and the pumps, the first frequency mode 210 being in the vicinity of about 50 Hz and the second frequency mode 220 being in the vicinity of about 80 Hz (e.g., in the example embodiments of FIGS. 2A-2C). In various embodiments, sources of vibrations that are internal to the opto-fluidic instrument (e.g., such as but not limited to the fluidics module) may vibrate at frequencies in the range from about 25 Hz to about 75 Hz, from about 30 Hz to about 65 Hz, from about 35 Hz to about 60 Hz, from about 40 Hz to about 55 Hz, about 50 Hz, from about 75 Hz to about 125 Hz, from about 85 Hz to about 115 Hz, from about 95 Hz to about 105 Hz, about 100 Hz, from about 50 Hz to about 100 Hz, including values and subranges therebetween.

Vibrations from external sources can have discrete frequency modes and/or very broad frequency ranges. For example, vibrations from pedestrian movements (e.g., walking, running, etc.), background environments, etc., have been found to have frequency values in the range from about 2 Hz to about 6 Hz, from about 2 Hz to about 4 Hz, from about 4 Hz to about 6 Hz, including values and subranges therebetween. On the other hand, vibrations due to shocks, bumps, or other sources of vibrations that have limited time span can have extended frequency ranges.

In various embodiments, the vibrations from the internal and/or external sources of vibrations can distort the 3D stack images of samples that are acquired by an optical imaging system of an opto-fluidic instrument. In some instances, the distortions can depend on the frequency of the vibrations and the rate at which the images of the 2D slices of the samples are acquired. For example, if the vibrational frequency is multiple (e.g., two, three, four, etc.) orders of magnitude larger than the 2D slice image capture rate (i.e., the event time of the vibrations is very short), then one of the predominant effects of the vibration can be the blurring of individual 2D slice images of the 3D stack images. That is, for instance, the event time of the vibration may be within the time that the imaging system is scanning a single 2D slice of a sample to image the slice, and in such cases, the 2D slice image may be distorted or blurred as a result of the vibrational disturbance. On the other hand, if the vibrational frequency is multiple (e.g., two, three, four, etc.) orders of magnitude smaller than the 2D slice image capture rate, then one of the predominant effects of the vibration can be the gradual drifting of 2D slice images with respect to each other, resulting in 2D slice images of a 3D stack images that fail to co-locate with each other.

In various embodiments, the frequency of the vibration can be comparable to the 2D slice image capture rate. For example, the vibrational frequency can be within a few (e.g., one or two) orders of magnitude of the 2D slice image capture rate. In such cases, one of the predominant effects of the vibration can be "stack shearing" where one or a few 2D slice images of the 3D stack image of a sample are displaced with respect to the rest of the 2D slice images. For example, a vibration may cause an XY-stage supporting a sample to be displaced laterally (e.g., in the XY plane) for a short period of time while an optical imaging system is acquiring multiple 2D slice images of the sample. In such cases, the one or more 2D slices of the sample that are imaged by the imaging system during the vibration may be displaced or shifted laterally due to the vibration. As a result, the one or more 2D slice images of these sample slices may then be laterally displaced or shifted with respect to the images of the 2D slices imaged before or after the vibration. The displaced 2D slices or images thereof, may be described as "stack-sheared" slices or images, respectively.

Figure 3:
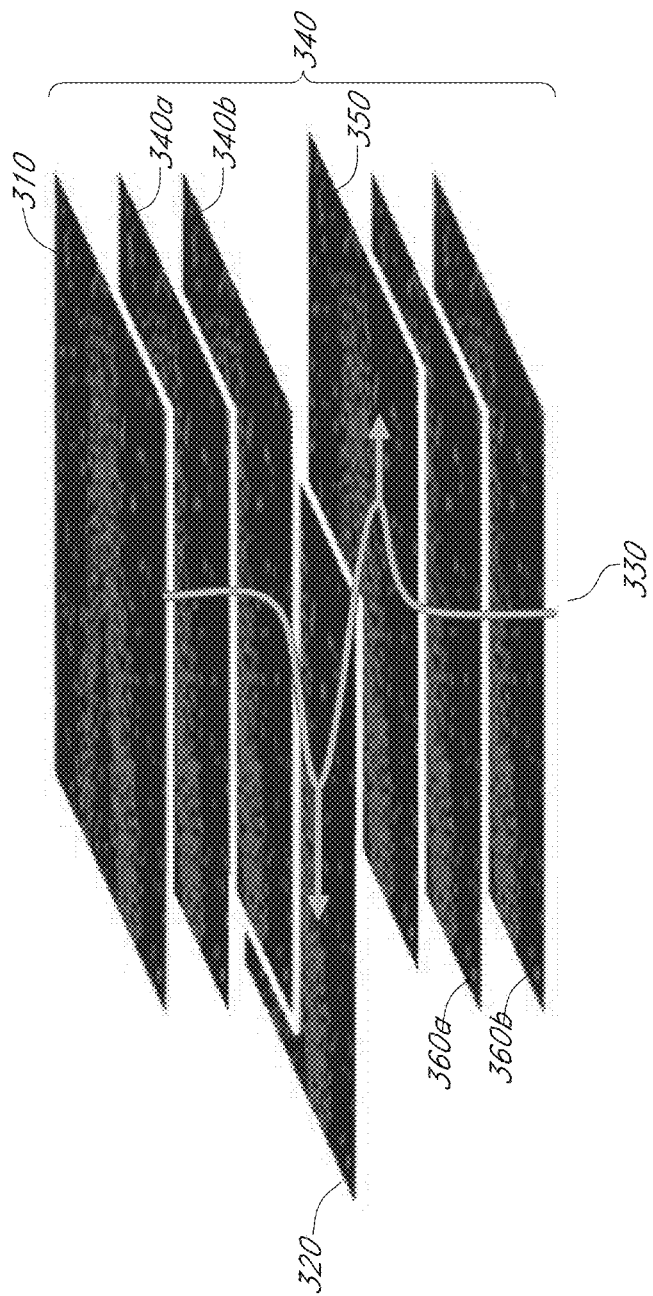
FIG. 3 illustrates stack shearing of a 2D slice image within a Z-stack due to a vibrational disturbance during the imaging of the sample, according to various embodiments.

FIG. 3 illustrates stack shearing where a vibration 330 causes 2D slice images 320, 350 of the 3D stack images 310 (e.g., comprising multiple 2D slice images including the displaced 2D slice images 320, 350) to fail to be co-located with the other 2D slice images of the 3D stack images 310, resulting in a shifted and/or distorted image of the sample. For instances, after an optical imaging system acquires 2D slice images 340a, 340b, an internal or external vibration (e.g., having a frequency that is comparable to the rate at which 2D slice images of the 3D stack images 310 are acquired) may cause an XY-stage supporting the sample to be displaced. In such cases, the sample, and the 2D slices thereof, may be laterally displaced, and the optical imaging system may acquire 2D slice images 320, 350 of these vibrationally displaced slices of the sample. In such cases, these 2D slice images 320, 350 that are captured during that time period may be stack shared with respect to the 2D slice images 340a, 340b that are imaged before the vibration, as well as 2D slice images 360a, 360b that may be acquired after the vibration dissipates. That is, 2D slice images 320, 350 are stack sheared or shifted with respect to the rest of the 2D slice images 340a, 340b, 360a, 360b that make up the 3D stack images 310. In various embodiments, shifting and/or distortion of one or more images causes image registration between slices to fail.

In some instances, the distortions to the 3D stack images 310 (e.g., the displacement or stack shearing of 2D slice images 320, 350) can be correctable. For example, the displacement or stack shearing of 2D slice images 320, 350 can be less than a threshold displacement above which the 3D stack images 310 may be deemed to be unacceptable. In such cases, the 3D stack images 310 may be corrected by shifting the 2D slice images 320, 350 (e.g., and/or features of interest depicted thereon such as fluorescent objects, etc., shown in the 2D slice images 320, 350) by the amount the 2D slice images 320, 350 are displaced. In some instances, correcting the 3D stack images 310 may refer to adjusting the position information associated with the 2D slice images 320, 350 and/or the 3D stack images 310. For example, the position information may include the locations of the 2D slice images 320, 350, the objects of interest depicted thereon, etc., and these locations may be shifted by the displacement amount (which may be referred herein alternatively as "offset"). In some instances, the displacement or stack shearing of 2D slice images 320, 350 can be greater than or equal to the threshold displacement, and in such cases, the 3D stack images 310 may be deemed to be unacceptable/uncorrectable and the sample may be re-imaged, i.e., another 3D stack image of the sample may be re-acquired. The amount the 2D slice images 320, 350 are displaced, which corresponds to the displacement of the sample during the vibration, may be measured by a position sensor that is coupled to the XY-stage supporting the sample.

In various embodiments, positional information is recorded by one or more encoders on the X-, Y-, and/or Z-stages during imaging of each slice. In various embodiments, the positional information is recorded from immediately before imaging begins until immediately after imaging ends (e.g., during substantially the entire exposure time for a particular channel). In various embodiments, exposure time is dependent on the particular channel being imaged (e.g., red, yellow, green, blue, ultraviolet, etc.). In various embodiments, the exposure time is about 1 ms to about 100 ms. In various embodiments, the exposure time is about 1 ms to about 90 ms. In various embodiments, the exposure time is about 1 ms to about 80 ms. In various embodiments, the exposure time is about 1 ms to about 70 ms. In various embodiments, the exposure time is about 1 ms to about 60 ms. In various embodiments, the exposure time is about 1 ms to about 50 ms. In various embodiments, the exposure time is about 1 ms to about 40 ms. In various embodiments, the exposure time is about 1 ms to about 30 ms. In various embodiments, the exposure time is about 1 ms to about 20 ms. In various embodiments, the exposure time is about 1 ms to about 10 ms. In various embodiments, the exposure time is about 1 ms to about 5 ms. In various embodiments, the exposure time is less than about 1 ms.

In various embodiments, a mean position is determined from the recorded positional information for one or more (e.g., all) of the images in the Z-stack. In various embodiments, during exposure, about 1 ms to about 2 ms of encoder data is recorded. In various embodiments, a median position is determined from the recorded positional information for one or more (e.g., all) of the images in the Z-stack. In various embodiments, a standard deviation is determined from the recorded positional information for one or more (e.g., all) of the images in the Z-stack. In various embodiments, the recorded positional information is associated with the respective image in the Z-stack to which the recorded positional information corresponds. In various embodiments, one or more statistics (e.g., mean, median, and/or standard deviation) of the positional information is associated with the respective image to which the statistics correspond. In various embodiments, the positional information and/or the statistics are contained within metadata of each image in the Z-stack. In various embodiments, the positional information corresponds to a fixed position within the image (e.g., top left corner, center, etc.).

In various embodiments, each 2D image obtained as a part of a Z-stack has an expected X, Y, and/or Z position. In various embodiments, when a vibrational disturbance occurs, the recorded X, Y, and/or Z-position of the image will deviate from the expected X, Y, and/or Z position. In various embodiments, when a vibrational disturbance is determined to have occurred during imaging of a 2D slice, the positional information associated with the image may be adjusted. In various embodiments, the positional information of the image obtained during the vibrational disturbance may be adjusted to be the expected X, Y, and/or Z position. In various embodiments, the positional information of the image(s) is adjusted when the vibrational disturbance is about 200 nm or more. In various embodiments, the positional information of the image(s) is adjusted when the vibrational disturbance is about 190 nm or more. In various embodiments, the positional information of the image(s) is adjusted when the vibrational disturbance is about 180 nm or more. In various embodiments, the positional information of the image(s) is adjusted when the vibrational disturbance is about 170 nm or more. In various embodiments, the positional information of the image(s) is adjusted when the vibrational disturbance is about 160 nm or more. In various embodiments, the positional information of the image(s) is adjusted when the vibrational disturbance is about 150 nm or more. In various embodiments, the positional information of the image(s) is adjusted when the vibrational disturbance is about 140 nm or more. In various embodiments, the positional information of the image(s) is adjusted when the vibrational disturbance is about 130 nm or more. In various embodiments, the positional information of the image(s) is adjusted when the vibrational disturbance is about 120 nm or more. In various embodiments, the positional information of the image(s) is adjusted when the vibrational disturbance is about 110 nm or more. In various embodiments, the positional information of the image(s) is adjusted when the vibrational disturbance is about 100 nm or more. In various embodiments, the positional information of the image(s) may be adjusted when the vibrational disturbance is about 90 nm or more. In various embodiments, the positional information of the image(s) may be adjusted when the vibrational disturbance is about 80 nm or more. In various embodiments, the positional information of the image(s) may be adjusted when the vibrational disturbance is about 70 nm or more. In various embodiments, the positional information of the image(s) may be adjusted when the vibrational disturbance is about 60 nm or more. In various embodiments, the positional information of the image(s) may be adjusted when the vibrational disturbance is about 50 nm or more. In various embodiments, the positional information of the image(s) may be adjusted when the vibrational disturbance is about 40 nm or more. In various embodiments, the positional information of the image(s) may be adjusted when the vibrational disturbance is about 30 nm or more. In various embodiments, the positional information of the image(s) may be adjusted when the vibrational disturbance is about 100 nm to about 200 nm. In various embodiments, the positional information of the image(s) may be adjusted when the vibrational disturbance is about 30 nm to about 200 nm.

The determination whether to correct the 3D stack images 310 (e.g., with the sheared 2D slice images 320, 350) or re-acquire another 3D stack image of the sample may be made based on the response of the XY-stage (e.g., and as such the sample thereon) to the vibration during the imaging of the sample. For example, the position sensor that is coupled to the XY-stage may be used to measure multiple positions of the XY-stage during the vibration. A processor of the opto-fluidic instrument may then compute the displacements of the XY-stage due to the vibration. The displacements may be computed as the differences between the multiple measured positions of the XY-stage and its nominal position (e.g., the position of the XY-stage in the absence of the vibration that caused the stack shearing). The processor can then compute the standard deviation of the multiple computed displacements. If the standard deviation is low (e.g., less than a threshold standard deviation) or high (e.g., greater than or equal to the threshold standard deviation), then the sheared 2D slice images 320, 350 may be viewed as accurate, or inaccurate, respectively, images of the 2D slices of the displaced sample during the vibration. In other words, the 3D stack images 310 may be viewed to be correctable or uncorrectable, respectively. This is because the low or high standard deviation may indicate that there is a low or high variation in the positions of the displaced sample during the vibration, and as such the 2D slice images 320, 350 of the 2D sample slices may be considered as accurate, or inaccurate, images of the (displaced) 2D sample slices, respectively.

Accordingly, the processor may compare the computed standard deviation to the standard deviation threshold to determine whether to correct the 3D stack images 310 or reacquire another 3D stack image of the sample. For example, if the standard deviation is less than the standard deviation threshold, the processor may determine to correct the 3D stack images 310, and if the standard deviation is greater than or equal to the standard deviation threshold, the processor may instruct the imaging system to re-image the sample. To correct the 3D stack images 310, the processor may first compute the average of the multiple positions of the displaced sample that are measured by the XY-stage during the imaging of a 2D slice of the sample to determine the average position of the displaced 2D slice. The processor may also compute the average of the multiple computed displacements to determine the average disablement or offset. The processor may then adjust or shift the average position by the average offset when the standard deviation is less than the threshold standard deviation (e.g., and when the average offset is less than the threshold displacement or offset).

V. Systems and Methods for Improving Imaging of Samples by Opto-Fluidic Instrument Various embodiments describe systems for improving imaging of samples by an opto-fluidic instrument. In at least one embodiment, a system comprises: an XY-stage configured to support a sample; an optical imaging system configured to acquire a first plurality of Z-stack images of a sample supported by an XY-stage, wherein the first plurality of Z-stack images are images of a respective plurality of two-dimensional (2D) slices of the sample; a position sensor coupled to the XY-stage and configured to measure a position of one of the plurality of 2D slices, wherein one of the first plurality of Z-stack images is an image of the one of the plurality of 2D slices; and a processor coupled to the position sensor and configured to: compute a position offset between the measured position and a nominal position, of the one of the plurality of 2D slices; and determine whether to adjust, using the processor, position information associated with the one of the first plurality of Z-stack images, or acquire, using the optical imaging system, a second plurality of Z-stack images of the sample based at least in part on a comparison of the position offset with a threshold offset.

In at least one aspect, which may be combined with other aspects described herein, the optical imaging system includes an epifluorescence microscope. In at least one aspect, which may be combined with other aspects described herein, the position sensor is an optical encoder. In at least one aspect, which may be combined with other aspects described herein, the system may further comprise a Z-stage coupled to the optical imaging system and configured to move an objective lens of the optical imaging system in the Z-direction. In at least one aspect, which may be combined with other aspects described herein, the position of one of the plurality of 2D slices includes an X-Y position of the one of the plurality of 2D slices; and the position sensor is coupled to the XY-stage and is configured to measure the X-Y position of the one of the plurality of 2D slices. In at least one aspect, which may be combined with other aspects described herein, the position of the one of the plurality of 2D slices includes a plurality of positions of the one of the plurality of 2D slices and the position offset includes a plurality of position offsets between the plurality of positions and the nominal position of the one of the plurality of 2D slices. Furthermore, the processor may be further configured to: compute a standard deviation of the plurality of position offsets.

In at least one aspect, which may be combined with other aspects described herein, the processor determines to adjust the position information when the computed standard deviation is less than a threshold standard deviation and the position offset is less than a threshold offset.

In at least one aspect, which may be combined with other aspects described herein, the processor determines to acquire the second plurality of Z-stack images when the computed standard deviation is equal to or greater than a threshold standard deviation and/or the position offset is equal to or greater than a threshold offset.

In at least one aspect, which may be combined with other aspects described herein, the measured position includes an x-direction measured position value ("MPV-x") and a y-direction measured position value ("MPV-y"), and the nominal position includes an x-direction nominal position value ("NPV-x") and a y-direction nominal position value ("NPV-y"); the position offset includes an x-direction offset ("OFF-x") between MPV-x and NPV-x and a y-direction offset ("OFF-y") between MPV-y and NPV-y; the one of the first plurality of Z-stack images depicts a fluorescent object; and the processor adjusts the position information by shifting an x-direction position of the fluorescent object by the OFF-x and/or a y-direction position of the fluorescent object by the OFF-y.

In at least one embodiment, a system comprises: a computing node comprising a computer readable storage medium having program instructions embodied therewith. The program instructions are executable by a processor to cause the processor to perform a method. The method comprises: receiving a first plurality of Z-stack images of a sample disposed on a stage; for each image in the plurality of Z-stack images: receiving one or more position measurements of the stage associated with the image; assigning the one or more position measurements to the image; determining at least one position offset between the one or more position measurements and a nominal position; and if the position offset is below a threshold offset, adjusting the one or more position measurements associated with the image if the position offset is above the threshold offset, providing an indication to an optical imaging system to acquire a second plurality of Z-stack images of the sample.

The following examples describe additional non-limiting embodiments based on the preceding embodiments.

Figure 4:
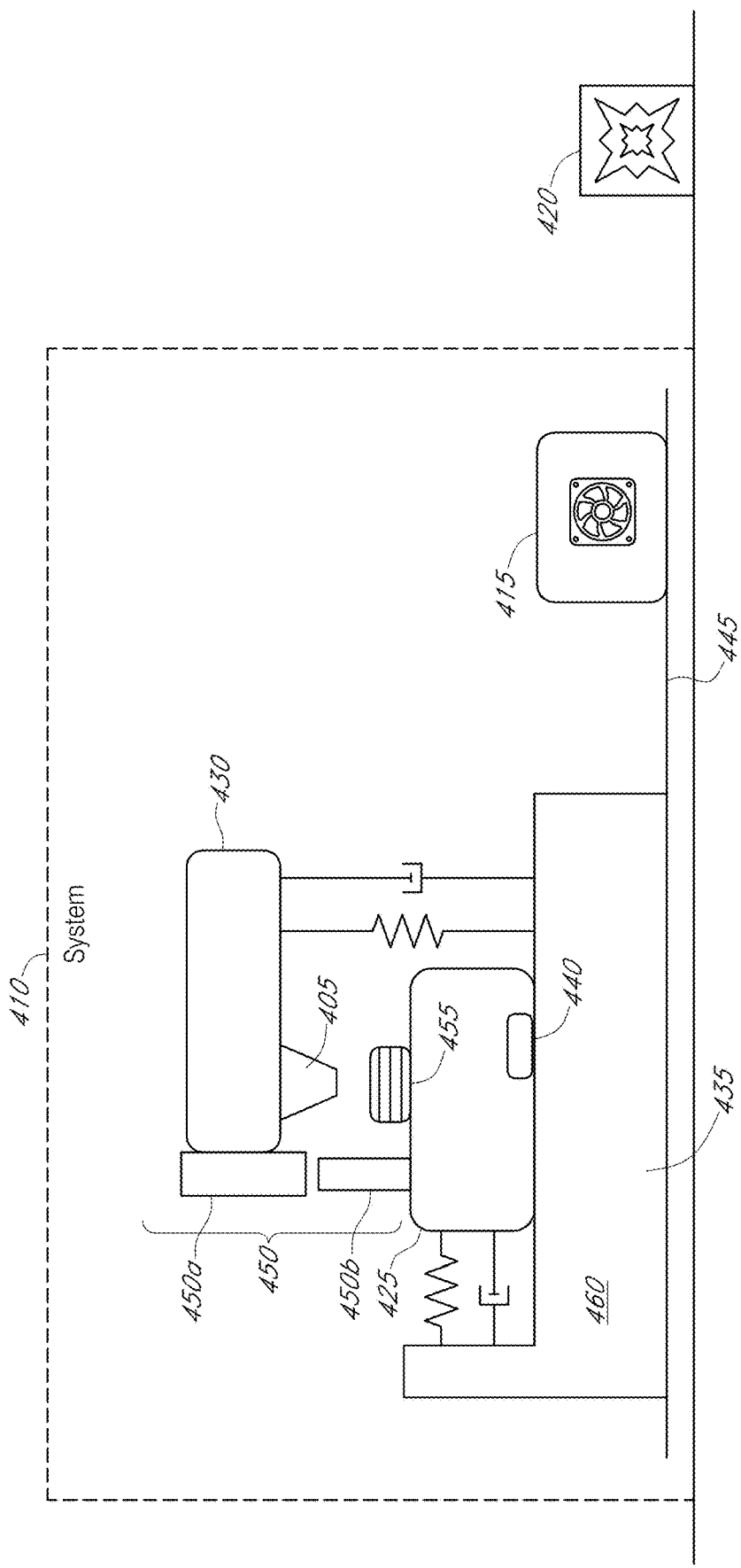
FIG. 4 shows an example illustration of a vibration mitigation system for improving the imaging of samples in opto-fluidic instruments, according to various embodiments.

FIG. 4 shows an example illustration of a system 410 for improving the imaging of samples by opto-fluidic instrument in the presence of vibrational disturbances, according to various embodiments. In various embodiments, the system 410 can be an opto-fluidic instrument that is the same as or substantially similar to the opto-fluidic instrument 120 of FIG. 1. The system 410 may include an internal source of vibration 415. For example, the internal source of vibration 415 can be a fluidics module that is the same or substantially similar to the fluidics module 140 of FIG. 1. The internal source of vibration 415 may include components therein such as but not limited to pumps, fans, etc., that may cause the internal source of vibration 415 to vibrate when in operation. Further, the system 410, and modules therein, may be subjected to vibrations that are triggered by an external source of vibrations 420. For example, the external source of vibrations can be the background environment, humans/objects in motion (e.g., walking, driving, etc.) in the vicinity of the system 410.

In various embodiments, the system 410 may include an XY-stage 425 that is configured to support a sample 455 to be imaged by an optical imaging system. The XY-stage 425 itself may be supported by a frame 435 and may be configured to move the sample 455 in the 2D plane (xy-direction) of the frame 435. In some instances, the optical imaging system may include an objective lens 405 that is positioned above the sample 455 and is supported by a Z-stage 430. In some instances, the Z-stage 430 may be configured to move the objective lens 405 in the vertical direction (e.g., bi-directionally) perpendicular to the 2D plane above the sample 455. In some instances, the XY-stage 425 may be coupled to the frame 435 such that vibrations from the internal source of vibration 415 and/or the external source of vibrations 420 may cause the XY-stage 425 to vibrate in the 2D plane of the frame 435 from its resting position on the frame 435. Similarly, the Z-stage 430 may be coupled to the frame 435 such that vibrations from the internal source of vibration 415 and/or the external source of vibrations 420 may cause the Z stage 430 to vibrate along the vertical direction (i.e., perpendicular to the 2D plane of the frame 435). In some instances, the frame 435 can be the optical frame of the optics module of the system, where the optics module may be the same or substantially similar to the optics module 150 of FIG. 1.

In various embodiments, the XY-stage 425 may be coupled to a position sensor 440 that is configured to sense or measure the two-dimensional position of the XY-stage 425 (e.g., and as such the sample 455 disposed thereon). For example, the position sensor 440 may sense or measure the position of the sample 455 and/or the XY-stage 425 with respect to any designated reference frame, such as a reference frame of the frame 435, the system 410, the chassis 445, etc. In some instances, the position sensor can be an optical encoder, a potentiometric position sensor, a capacitive position sensor, a fiber-optic position sensor, an ultrasonic position sensor, and/or the like. In various embodiments, the Z-stage may also be coupled to a position sensor 450 that is configured to sense or measure the height of the objective lens 405 and/or the Z-stage 430 from the sample 455. That is, the position sensor 450 may be configured to measure the separation distance between the objective lens 405 and/or the Z-stage 430 and the sample 455 and/or the XY-stage 425 on which the sample is located.

For example, the position sensor 450 can be a capacitive position sensor that includes a capacitive position sensor target 450a and a capacitive sensor probe 450b. Although FIG. 4 shows the position sensor 450 as a capacitive position sensor, it is to be understood as a non-limiting example and that the position sensor 450 can also be any other types of position sensor including but not limited to an optical encoder, a potentiometric position sensor, a fiber-optic position sensor, an ultrasonic position sensor, and/or the like. In some of these instances, the position sensor 450 may measure the height of the objective lens 405 and/or the Z-stage 430 with respect to some reference frame, such as a reference frame of the frame 435, the system 410, the chassis 445, etc. (from which the afore-mentioned separation distance may be determined).

Figure 5C:
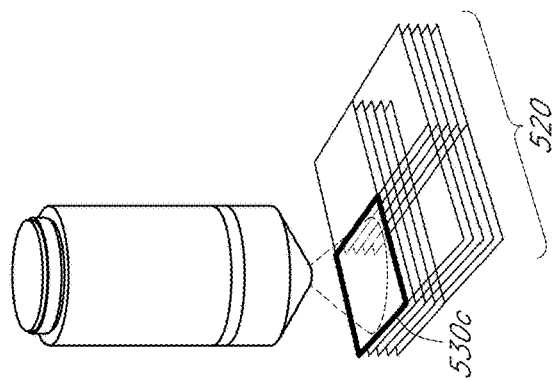
FIGS. 5A-5C shows an example illustration of Z-stack imaging of a sample by an opto-fluidic instrument, according to various embodiments.
Figure 5B:
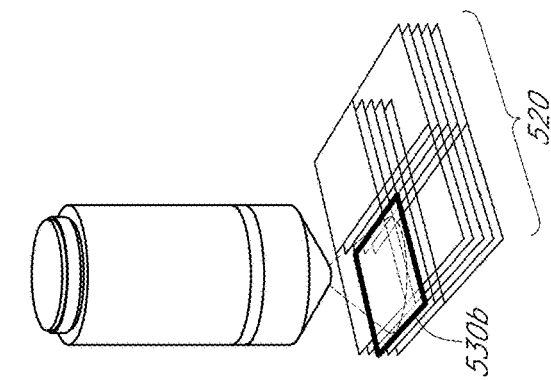
Figure 5A:
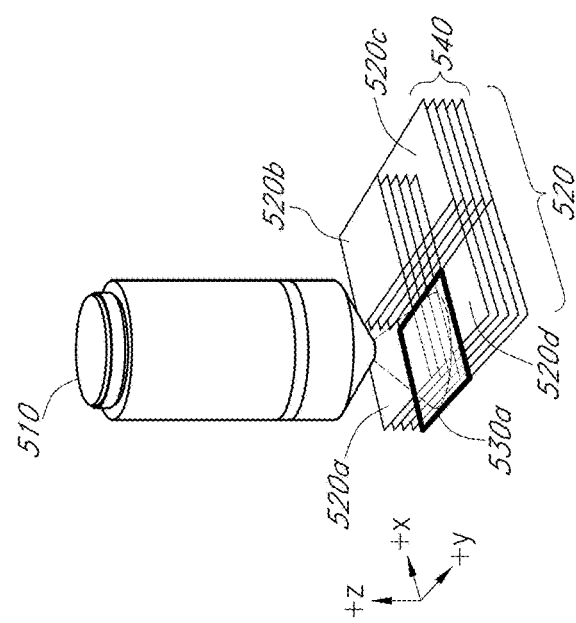

The imaging of the sample 455 by the optical imaging system may be illustrated with reference to FIGS. 5A-5C, where the sample 520 corresponds to sample 455 of FIG. 4. In various embodiments, the optical imaging system 510 may be positioned vertically above the sample 520. In some instances, the field of view (FOV) of the optical imaging system 510 may be smaller than the sample 520. In such cases, the optical imaging system 510 may be configured to acquire 3D Z-stack images of sections 520a, 520b, 520c, 520d of the sample at a time, where a section's size is such that the section falls within the FOV of the optical imaging system. For instance, FIGS. 5A-5C indicate that the 2D dimensions of the sample 520 extend beyond the FOV of the optical imaging system 510, and as such, for imaging purposes, the sample 520 may be divided into four sample sections 520a, 520b, 520c, 520d, each of which the optical imaging system 510 can image separately. That is, the optical imaging system may acquire 3D Z-stack images of each sample section 520a, 520b, 520c, 520d separately. In some instances, once 3D Z-stack images of a first sample section 520a are acquired, the XY-stage (e.g., same as or similar to the XY-stage 425) supporting the sample 520 may move in the x and/or y-direction (i.e., in the 2D plane of the frame 435) to allow the optical imaging system to acquire 3D Z-stack images of the other sample sections 520b, 520c, 520d. For example, after the 3D Z-stack images of the first sample section 520a are acquired, the XY-stage may move in the x- or y-direction to bring the other sample sections 520b, 520c, 520d within the FOV of the optical imaging system 510 so that the optical imaging system 510 may acquire 3D Z-stack images of each of sample sections 520b, 520c, 520d.

In acquiring 3D Z-stack images of a sample or section of the sample, in various embodiments, the optical imaging system 510 may traverse along the vertical Z-direction at regular interval so that the focal plane of the objective lens of the optical imaging system 510 coincides with 2D slices of the sample or sample section, which the optical imaging system then images. For example, the optical image 510 may be positioned above the sample section 520a at such a height that the focal plane of the objective lens may coincide with one 2D slice 530a of the multiple 2D slices 540 of the sample section 520a. After the optical imaging system 510 captures an image of the 2D slice 530a, the objective lens may move vertically by a prescribed distance such that its focal plane coincides with another 2D slice 530b of the sample section 520a. In some instances, the prescribed distance can be determined from measurements of a position sensor (e.g. such as the capacitive position sensor 450a and 450b of FIG. 4), and can be in the range from about 500 nm to about 1000 nm, from about 600 nm to about 900 nm, from about 650 nm to about 800 nm, from about 700 nm to about 750 nm, about 750 nm, including values and subranges therebetween. In various embodiments, a step distance between each 2D sample slice in the Z-stack of images is equal to the z-resolution of the optical system. The movement of the objective lens may be effected by the Z-stage that supports the objective lens. The optical imaging system 510 may then acquire a 2D image of the 2D slice 530b of the sample section 520a (FIG. 5B). The optical imaging system 510 may then repeat the process acquire a 2D image of the 2D slice 530c of the sample 520a (FIG. 5C) to acquire 2D images of the multiple slices 540 of the sample section 520a to which the focal plane of the objective lens coincides. The acquired 2D images of the 2D slices 540 of the sample section 520a may then constitute the 3D Z-stack images of the sample section 520a.

In various embodiments, vibrations from internal as well as external sources of vibration can cause the XY-stage supporting the sample 520 to vibrate in the xy-direction, which can cause the 3D Z-stack images of the sample 520 to be inaccurate or distorted. For example, the frequencies of the vibrations can be within a few (e.g., one or two) orders of magnitude of the image capture rate at which the optical imaging system acquires each 2D slice image of the 3D Z-stack images. In such cases, one or more 2D slices may be displaced with respect to the rest of the 2D slices when being imaged, i.e., the one or more 2D slice images may be sheared and may not be co-located with respect to the rest of the 2D slice images of the 3D Z-stack images. For instance, as noted above, a vibration from an internal or external source can cause the XY-stage to vibrate in the xy-direction at a frequency within a few orders of magnitude of the of the image capture rate of the optical imaging device. In such cases, some of the 2D images in the 3D Z-stack images may be images of 2D slices of the sample section 520a that are displaced in the xy-direction (e.g., with respect to 2D slices of the sample section 520a that are imaged in the absence of the vibrations). As such, the 2D images acquired in the presence of vibration may be sheared, i.e., not co-located, with respect to the 2D images acquired in the absence of vibrations (e.g., similar to 2D slice images 320, 350 in FIG. 3 which are stack-sheared images of displaced 2D slices of a sample. The 2D slice images 320, 350 in FIG. 3 are acquired when the sample, and as such the 2D slices, were displaced as a result of vibrations 330 of the XY-stage in the xy-directions). In other words, the 3D Z-stack images of the multiple 2D slices 540 of the sample section 520a may be distorted and inaccurate.

Returning to FIG. 4, in various embodiments, the system 410 may include a system controller 460 (e.g., same as or similar to system controller 130 of FIG. 1) that can be utilized to determine whether to correct, or re-acquire, the 3D Z-stack images of the sample 455, or section thereof (referred hereinafter simply as "sample" for brevity). Further, the system 410 may also utilize the position sensor 440 in performing the same determination. In various embodiments, the position sensor 440 may measure real-time 2D plane/xy-direction position measurements (referred hereinafter simply as "position measurements") of the XY-stage 425 (e.g., and as such real-time position measurements of the sample 455) while the optical imaging system is capturing 3D-stack images of the sample 455. In some instances, as noted above, the position sensor may measure the position of the sample 455 with respect to any designated reference frame, such as a reference frame of the frame 435, the system 410, the chassis 445, etc. The position sensor 440 may then transmit the position measurements to the system controller 460.

Upon receiving the position measurements, in various embodiments, the system controller 460 may compute the position shifts or offsets (e.g., displacements in the xy-directions) of the displaced 2D slices of the sample 455 due to the vibrations that caused the stack-shearing. In some instances, the shifts or offsets may be with respect to the nominal or target positions of those 2D slices of the sample 455, which are the positions the 2D slices would have had in the absence of the vibrations. For example, if the two-dimensional (in the xy-directions) nominal or target position of a 2D slice of the sample 455 is $(x_0, y_0)$ and the xy-position of that 2D slice as measured by the position sensor 440 is $(x_1, y_1)$, then the position offset of the 2D slice may be determined by computing the difference between measured position and the nominal position, i.e., offset=$(off_x, off_y)$= $(x_1-x_0, y_1-y_0)$.

In various embodiments, the system controller 460 may determine whether to correct, or re-acquire, 3D Z-stack images of the sample 455 based at least in part on a comparison of the position offset and a threshold offset. In some instances, correcting the 3D Z-stack images may include adjusting the position information associated with the displaced 2D slices of the sample 455. For example, each 2D image of the 3D Z-stack images may depict various features such as but not limited to fluorescent objects. In such cases, the position information may be the positions of these features (e.g., with respect to the sample 455 itself or the reference frames used to measure the positions of the sample 455), and adjusting the position information associated with the displaced 2D slices of the sample 455 may include shifting the positions of the fluorescent objects in the displaced 2D slices by the offset. In some instances, such a shift may restore the florescent objects to their nominal positions on the 2D images, which allows the initially displaced 2D images to be co-located with the 2D images of the 3D Z-stack images that were acquired in the absence of the vibrations that caused the displacement.

In various embodiments, the threshold offset $(x_{th}, y_{th})$ may be the maximum displacement for a 2D slice of a sample 455 for which the 3D Z-stack images of the sample 455 may be considered correctable. In some instances, the comparison may indicate that the position offset is less than the threshold offset, and in such cases, the system controller 460 may correct the 3D Z-stack images of the sample 455 (e.g., by adjusting the position information associated with the displaced 2D slices of the sample 455). In some cases, the comparison may indicate that the position offset is equal to or greater than the threshold offset, and in such cases, the system controller 460 may instruct the optical imaging system to re-acquire the 3D Z-stack images of the sample 455.

In some instances, the position offset being less than to the threshold offset may refer to both of the following conditions being fulfilled: $off_x < x_{th}$ and $off_y < y_{th}$. In some instances, the position offset being equal to the threshold offset may refer to both of the following conditions being fulfilled: $off_x = x_{th}$ and $off_y = y_{th}$. In some instances, the position offset being greater than the threshold offset may refer to one or both of the following conditions being fulfilled: $off_x = x_{th}$ or $off_y = y_{th}$. In some instances, the threshold offset may be a scalar value, i.e., a threshold offset distance din. In such cases, the position offset being less than, equal to, or greater than the threshold offset may refer to $(x_{th}^2+y_{th}^2)^{0.5}<d_{th}$, $(x_{th}^2+y_{th}^2)^{0.5}=d_{th}$, or $(x_{th}^2+y_{th}^2)^{0.5}>d_{th}$, respectively.

In various embodiments, the position sensor 440 may perform multiple position measurements of the sample 455 when an optimal imaging system is acquiring a single 2D image of a slice of the sample 455. For example, the position sensor 440 may perform position measurements at a much higher rate than the 2D slice image capture rate of the optical imaging device. In such cases, the position sensor 440 may collect several position measurements of the sample 455 during the imaging of the slice of the sample. For instance, the position sensor 440 may measure the position of the sample (e.g., and as such the position of the 2D slice) at a rate ranging from about 500 Hz to about 10 KHz (e.g., 500 Hz to about 1500 Hz), from about 750 Hz to about 1250 Hz, from about 900 Hz to about 1100 Hz, about 1000 Hz, including values and subranges therebetween. In various embodiments, the position sensor 440 measures the position of the sample at a rate ranging from about 500 Hz to about 10 kHz When the 2D slice image capture rate is in the range from about 10 Hz to about 20 Hz, and the 2D image capture rate is about 1000 Hz, then the position sensor 440 may have from about 50 to about 100 data points for the position of the sample 455 (e.g., and the slice).

In such instances, the system controller 460 may compute the position offsets between the multiple positions measurements and the nominal position of the sample. With respect to the above example, for instance, the system controller 460 may compute the differences between the position data points and the nominal position of the sample (e.g., the position of the sample in the absence of vibrations that cause the position offsets) to obtain multiple position offsets of the sample. The system controller 460 may then compute the average of the multiple position offsets and assign or consider the computed average as the position offset of the sample 455. Further, the system controller 460 may compute a standard deviation of the multiple position offsets and compare the computed standard deviation with a threshold standard deviation. The threshold standard deviation may be the maximum standard deviation for which the computed average position offset may be considered to be accurate.

In various embodiments, the system controller 460 may determine whether to correct, or re-acquire, the 3D Z-stack images of the sample 455 based on a comparison of the computed standard deviation to the maximum standard deviation. For example, the computed standard deviation associated with the displaced 2D slices of the sample 455 may be less than, or equal to and greater than, the threshold standard deviation, and in such cases, the system controller 460 may correct the 3D Z-stack images of the sample 455 (e.g., by adjusting the position information associated with the displaced 2D slices of the sample 455, or instruct the optical imaging system to re-acquire the 3D Z-stack images of the sample 455, respectively.

In some instances, the system controller 460 may determine whether to correct, or re-acquire, the 3D Z-stack images of the sample 455 based on both the position offset of the displaced 2D slices of the sample 455 and the computed standard deviation associated therewith. For example, the system controller 460 may perform the determination based on both comparisons of the position offset to the threshold offset and the standard deviation to the threshold standard deviation. For example, the system controller 460 may determine to adjust the position information associated with the displaced 2D slices when the computed standard deviation is less than a threshold standard deviation and the position offset is less than a threshold offset. As another example, the system controller 460 may determine to reacquire the 3D Z-stack images of the sample 455 when the computed standard deviation is equal to or greater than a threshold standard deviation and/or the position offset is equal to or greater than a threshold offset.

Various embodiments describe methods for improving the imaging of samples by an opto-fluidic instrument. In at least one embodiment, a method comprises: acquiring, using an optical imaging system, a first plurality of Z-stack images of a sample supported by an XY-stage, wherein the first plurality of Z-stack images are images of a respective plurality of two-dimensional (2D) slices of the sample; measuring, using a position sensor coupled to the XY-stage, a position of one of the plurality of 2D slices, wherein one of the first plurality of Z-stack images is an image of the one of the plurality of 2D slices; computing, using a processor coupled to the position sensor, a position offset between the measured position and a nominal position, of the one of the plurality of 2D slices; and determining whether to adjust, using the processor, the position information associated with the one of the first plurality of Z-stack images, or acquire, using the optical imaging system, a second plurality of Z-stack images of the sample, based at least in part on a comparison of the position offset and a threshold offset.

In at least one aspect, which may be combined with other aspects described herein, the optical imaging system includes an epifluorescence microscope.

In at least one aspect, which may be combined with other aspects described herein, the optical imaging system includes an epifluorescence microscope.

In at least one aspect, which may be combined with other aspects described herein, the acquiring the first plurality of Z-stack images includes moving the sample in X-direction or Y-direction using the XY-stage during the acquiring of the first plurality of Z-stack images by the optical imaging system.

In at least one aspect, which may be combined with other aspects described herein, the acquiring the first plurality of Z-stack images occurs at a rate ranging from about 10 Hz to about 70 Hz. In at least one aspect, which may be combined with other aspects described herein, the acquiring the first plurality of Z-stack images occurs at a rate ranging from about 10 Hz to about 20 Hz.

In at least one aspect, which may be combined with other aspects described herein, the measuring the position of one of the plurality of 2D slices occurs at a rate ranging from about 500 Hz to about 10 KHz.

In at least one aspect, which may be combined with other aspects described herein, the successive 2D slices of the plurality of 2D slices are separated from each other by a distance ranging from about 500 nm to about 1000 nm.

In at least one aspect, which may be combined with other aspects described herein, the position sensor is an optical encoder.

In at least one aspect, which may be combined with other aspects described herein, the position sensor is a potentiometric position sensor, a capacitive position sensor, a fiber-optic position sensor, or an ultrasonic position sensor.

In at least one aspect, which may be combined with other aspects described herein, the optical imaging system is coupled to a Z-stage configured to move an objective lens of the optical imaging system in the Z-direction.

In at least one aspect, which may be combined with other aspects described herein, the acquiring the first plurality of Z-stack images includes moving, using the Z-stage, the objective lens of the optical imaging system in the Z-direction during the acquiring of the first plurality of Z-stack images by the optical imaging system.

In at least one aspect, which may be combined with other aspects described herein, the position of one of the plurality of 2D slices includes an X-Y position of the one of the plurality of 2D slices; and the position sensor is coupled to the XY-stage and is configured to measure the X-Y position of the one of the plurality of 2D slices.

In at least one aspect, which may be combined with other aspects described herein, the plurality of 2D slices correspond to focal planes of an objective lens of the optical imaging system.

In at least one aspect, which may be combined with other aspects described herein, the determining includes determining to adjust the position information when the position offset is less than a threshold offset.

In at least one aspect, which may be combined with other aspects described herein, determining to acquire the second plurality of Z-stack images when the position offset is equal to or greater than the threshold offset.

In at least one aspect, which may be combined with other aspects described herein, the position of the one of the plurality of 2D slices includes a plurality of positions of the one of the plurality of 2D slices and the position offset includes a plurality of position offsets between the plurality of positions and the nominal position of the one of the plurality of 2D slices, the method further comprising: computing, using the processor, a standard deviation of the plurality of positions offsets.

In at least one aspect, which may be combined with other aspects described herein, the determining includes determining to adjust the position information when the computed standard deviation is less than a threshold standard deviation and the position offset is less than a threshold offset.

In at least one aspect, which may be combined with other aspects described herein, the determining includes determining to acquire the second plurality of Z-stack images when the computed standard deviation is equal to or greater than a threshold standard deviation and/or the position offset is equal to or greater than a threshold offset.

In at least one aspect, which may be combined with other aspects described herein, the measured position includes an x-direction measured position value ("MPV-x"), and a y-direction measured position value ("MPV-y"), and the nominal position includes an x-direction nominal position value ("NPV-x"), and a y-direction nominal position value ("NPV-y"); the position offset includes an x-direction offset ("OFF-x") between MPV-x and NPV-x, and a y-direction offset ("OFF-y") between MPV-y and NPV-y; the threshold offset includes an x-direction threshold offset ("TO-x") and a y-direction threshold offset ("TO-y"); and the position offset being less than the threshold offset includes the OFF-x and the OFF-y being less than the TO-x and the TO-y, respectively.

In at least one aspect, which may be combined with other aspects described herein, the measured position includes an x-direction measured position value ("MPV-x"), and a y-direction measured position value ("MPV-y"), and the nominal position includes an x-direction nominal position value ("NPV-x"), and a y-direction nominal position value ("NPV-y"); the position offset includes an x-direction offset ("OFF-x") between MPV-x and NPV-x, and a y-direction offset ("OFF-y") between MPV-y and NPV-y; the threshold offset includes an x-direction threshold offset ("TO-x") and a y-direction threshold offset ("TO-y"); and the position offset being equal to or greater than the threshold offset includes the OFF-x and the OFF-y, or a z-direction offset ("OFF-z") being equal to or greater than the TO-x, the TO-y, or a z-direction threshold offset ("TO-z"), respectively.

In at least one aspect, which may be combined with other aspects described herein, the measured position includes an x-direction measured position value ("MPV-x") and a y-direction measured position value ("MPV-y"), and the nominal position includes an x-direction nominal position value ("NPV-x") and a y-direction nominal position value ("NPV-y"); the position offset includes an x-direction offset ("OFF-x") between MPV-x and NPV-x and a y-direction offset ("OFF-y") between MPV-y and NPV-y; and the position offset being less than or greater than the threshold offset includes $((OFF\text{-}x)^2+(OFF\text{-}y)^2)^{0.5}$ being less than the threshold offset.

In at least one aspect, which may be combined with other aspects described herein, the measured position includes an x-direction measured position value ("MPV-x") and a y-direction measured position value ("MPV-y"), and the nominal position includes an x-direction nominal position value ("NPV-x") and a y-direction nominal position value ("NPV-y"); the position offset includes an x-direction offset ("OFF-x") between MPV-x and NPV-x and a y-direction offset ("OFF-y") between MPV-y and NPV-y; and the position offset being less than or greater than the threshold offset includes $((OFF\text{-}x)^2+(OFF\text{-}y)^2)^{0.5}$ being equal to or greater than the threshold offset.

In at least one aspect, which may be combined with other aspects described herein, the measured position includes an x-direction measured position value ("MPV-x") and a y-direction measured position value ("MPV-y"), and the nominal position includes an x-direction nominal position value ("NPV-x") and a y-direction nominal position value ("NPV-y"); the position offset includes an x-direction offset ("OFF-x") between MPV-x and NPV-x and a y-direction offset ("OFF-y") between MPV-y and NPV-y; the one of the first plurality of Z-stack images depicts a fluorescent object; and the adjusting the position information includes shifting an x-direction position of the fluorescent object by the OFF-x and/or a y-direction position of the fluorescent object by the OFF-y.

The following examples describe additional non-limiting embodiments based on the preceding embodiments.

Figure 6:
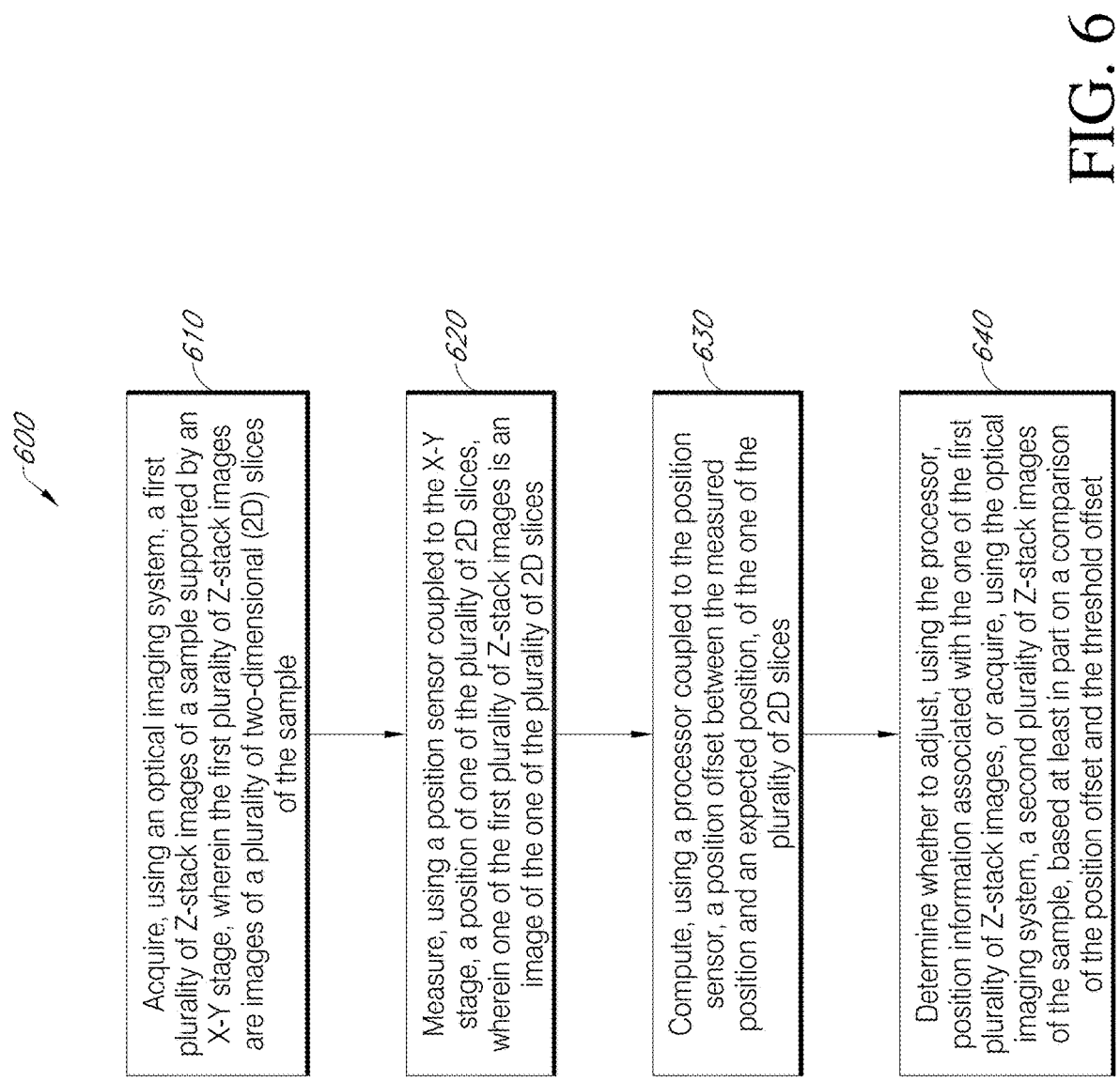
FIG. 6 is a flowchart illustrating an example method for improving the imaging of samples by an opto-fluidic instrument, according to various embodiments.

FIG. 6 is a flowchart illustrating an example method 600 for improving the imaging of samples by an opto-fluidic instrument, according to various embodiments. Aspects of the method 600 can be executed by the optics module 150, the sample module 160, the system controller 130, of FIG. 1, and/or other suitable means for performing the steps. As illustrated, the method 600 includes a number of enumerated steps, but aspects of the method 600 may include additional steps before, after, and in between the enumerated steps. In some embodiments, one or more of the enumerated steps may be omitted or performed in a different order.

At block 610, in various embodiments, an optical imaging system may acquire a first plurality of Z-stack images of a sample supported by an XY-stage. In some instances, the first plurality of Z-stack images may be acquired at a rate ranging from about 10 Hz to about 20 Hz. In some instances, the first plurality of Z-stack images may be acquired at a rate ranging from about 10 Hz to about 30 Hz. In some instances, the first plurality of Z-stack images may be acquired at a rate ranging from about 10 Hz to about 40 Hz. In some instances, the first plurality of Z-stack images may be acquired at a rate ranging from about 10 Hz to about 50 Hz. In some instances, the first plurality of Z-stack images may be acquired at a rate ranging from about 10 Hz to about 60 Hz. In some instances, the first plurality of Z-stack images may be acquired at a rate ranging from about 10 Hz to about 70 Hz. In some instances, the first plurality of Z-stack images may be acquired at a rate of at least 70 Hz. In some instances, acquiring the first plurality of Z-stack images includes moving the sample in X-direction or Y-direction using the XY-stage during the acquiring of the first plurality of Z-stack images by the optical imaging system. In some instances, the optical imaging system can be coupled to a Z-stage configured to move an objective lens of the optical imaging system in the Z-direction. In such cases, acquiring the first plurality of Z-stack images can include moving, using the Z-stage, the objective lens of the optical imaging system in the Z-direction during the acquiring of the first plurality of Z-stack images by the optical imaging system. In some instances, the first plurality of Z-stack images can be images of a plurality of two-dimensional (2D) slices of the sample. In some instances, the plurality of 2D slices correspond to focal planes of an objective lens of the optical imaging system. In some instances, successive 2D slices of the plurality of 2D slices may be separated from each other by a distance ranging from about 500 nm to about 1000 nm. In some instances, the optical imaging system includes an epifluorescence microscope.

At block 620, in various embodiments, a position sensor coupled to the XY-stage may measure a position of one of the plurality of 2D slices. In some instances, the position of one of the plurality of 2D slices may include an X-Y position. In such cases, the position of one of the plurality of 2D slices includes an X-Y position of the one of the plurality of 2D slices; and the position sensor is coupled to the XY-stage and is configured to measure the X-Y position of the one of the plurality of 2D slices. In some instances, the position sensor can be an optical encoder. In some instances, the position sensor can be a potentiometric position sensor, a capacitive position sensor, a fiber-optic position sensor, and/or an ultrasonic position sensor. In some instances, the position measurement of one of the plurality of 2D slices may occur at a rate ranging from about 500 Hz to about 10 KHz (e.g., 500 Hz to about 1500 Hz). In some instances, one of the first plurality of Z-stack images can be an image of the one of the plurality of 2D slices.

At block 630, in various embodiments, a processor coupled to the position sensor may compute a position offset between the measured position and an expected position, of the one of the plurality of 2D slices.

At block 640, in various embodiments, the processor may determine whether to adjust, using the processor, position information associated with the one of the first plurality of Z-stack images, or acquire, using the optical imaging system, a second plurality of Z-stack images of the sample, based at least in part on a comparison of the position offset and the threshold offset. In various embodiments, the determining includes determining to adjust the position information when the position offset is less than a threshold offset. In various embodiments, the determining includes determining to acquire the second plurality of Z-stack images when the position offset is equal to or greater than the threshold offset.

In various embodiments of method 600, the position of the one of the plurality of 2D slices includes a plurality of positions of the one of the plurality of 2D slices and the position offset includes a plurality of position offsets between the plurality of positions and the nominal position of the one of the plurality of 2D slices. In such cases, the method 600 further comprises computing, using the processor, a standard deviation of the plurality of position offsets. In some of such embodiments, the determining includes determining to adjust the position information when the computed standard deviation is less than a threshold standard deviation and the position offset is less than a threshold offset. In some of such embodiments, the determining includes determining to acquire the second plurality of Z-stack images when the computed standard deviation is equal to or greater than a threshold standard deviation and/or the position offset is equal to or greater than a threshold offset.

Figure 7:
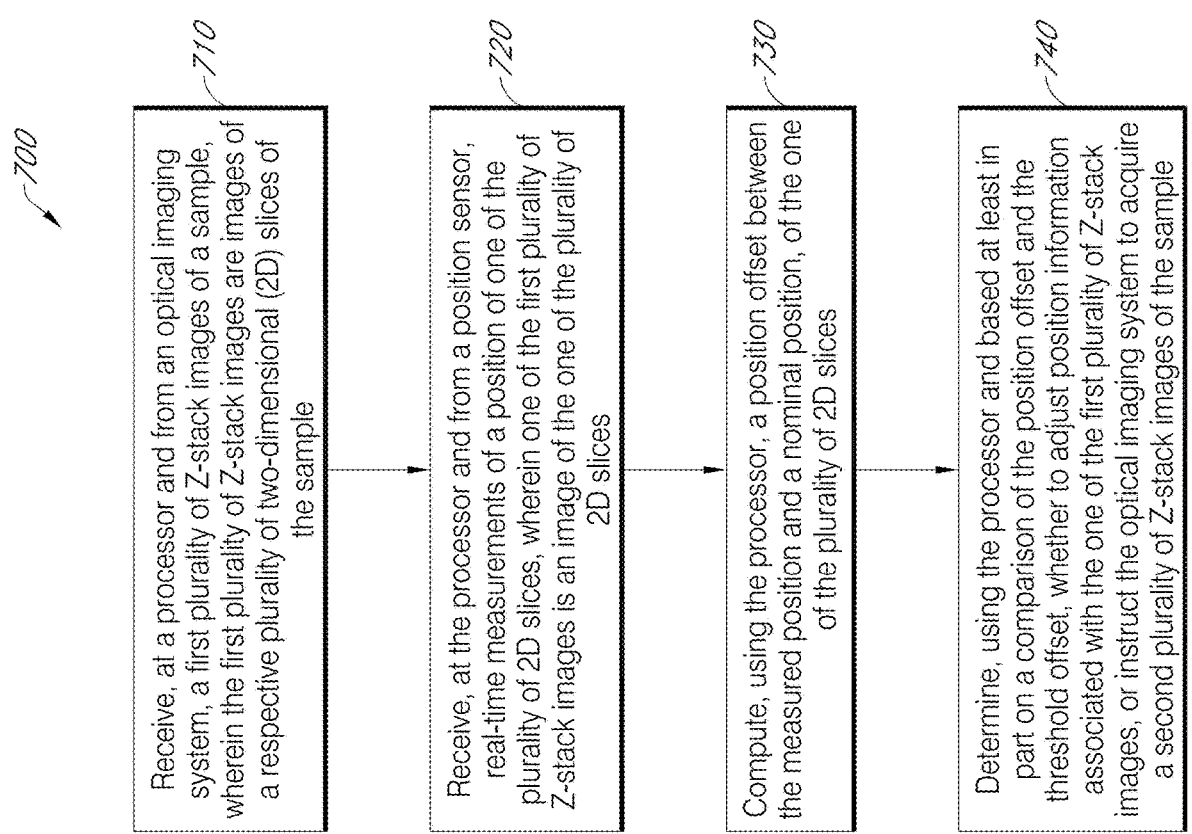
FIG. 7 is a flowchart illustrating an example method for improving the imaging of samples by an opto-fluidic instrument, according to various embodiments.

FIG. 7 is a flowchart illustrating an example method 700 for improving the imaging of samples by an opto-fluidic instrument, according to various embodiments. Aspects of the method 700 can be executed by the optics module 150, the sample module 160, the system controller 130, of FIG. 1, and/or other suitable means for performing the steps. As illustrated, the method 700 includes a number of enumerated steps, but aspects of the method 700 may include additional steps before, after, and in between the enumerated steps. In some embodiments, one or more of the enumerated steps may be omitted or performed in a different order.

At block 710, a processor (e.g., a processor of the system controller 130) may receive, from an optical imaging system, a first plurality of Z-stack images of a sample, wherein the first plurality of Z-stack images are images of a respective plurality of two-dimensional (2D) slices of the sample.

At block 720, the processor may receive from a position sensor, real-time measurements of a position of one of the plurality of 2D slices, wherein one of the first plurality of Z-stack images is an image of the one of the plurality of 2D slices.

At blocks 730, the processor may compute a position offset between the measured position and a nominal position, of the one of the plurality of 2D slices.

At block 740, the processor may determine, based at least in part on a comparison of the position offset and the threshold offset, whether to adjust position information associated with the one of the first plurality of Z-stack images, or instruct the optical imaging system to acquire a second plurality of Z-stack images of the sample. In various embodiments, the determining includes determining to adjust the position information when the position offset is less than a threshold offset. In various embodiments, the determining includes determining to acquire the second plurality of Z-stack images when the position offset is equal to or greater than the threshold offset.

In various embodiments of method 700, the position of the one of the plurality of 2D slices includes a plurality of positions of the one of the plurality of 2D slices and the position offset includes a plurality of position offsets between the plurality of positions and the nominal position of the one of the plurality of 2D slices. In such cases, the processor may compute a standard deviation of the plurality of position offsets. In such cases, the processor may determine to adjust the position information when the computed standard deviation is less than a threshold standard deviation and the position offset is less than a threshold offset. Further, the processor may determine to instruct the optical imaging system to acquire the second plurality of Z-stack images when the computed standard deviation is equal to or greater than a threshold standard deviation and/or the position offset is equal to or greater than a threshold offset.

In various embodiments of method and/or 700, the measured position includes an x-direction measured position value ("MPV-x"), and a y-direction measured position value ("MPV-y"), and the nominal position includes an x-direction nominal position value ("NPV-x"), and a y-direction nominal position value ("NPV-y"). Further, the position offset includes an x-direction offset ("OFF-x") between MPV-x and NPV-x, and a y-direction offset ("OFF-y") between MPV-y and NPV-y. In addition, the threshold offset includes an x-direction threshold offset ("TO-x") and a y-direction threshold offset ("TO-y"). In such cases, the position offset being less than the threshold offset includes OFF-x and OFF-y being less than TO-x and TO-y, respectively. Further, the position offset being equal to or greater than the threshold offset includes OFF-x and OFF-y, or a z-direction offset (OFF-z) being equal to or greater than TO-x, TO-y, or a z-direction threshold offset (TO-z), respectively.

In various embodiments of method 600 and/or 700, the measured position includes an x-direction measured position value ("MPV-x") and a y-direction measured position value ("MPV-y"), and the nominal position includes an x-direction nominal position value ("NPV-x") and a y-direction nominal position value ("NPV-y"). Further, the position offset includes an x-direction offset ("OFF-x") between MPV-x and NPV-x and a y-direction offset ("OFF-y") between MPV-y and NPV-y. In such cases, the position offset being less than or greater than the threshold offset includes $((OFF-x)^2+(OFF-y)^2)^{0.5}$ being less than the threshold offset. Further, the position offset being less than or greater than the threshold offset includes $((OFF-x)^2+(OFF-y)^2)^{0.5}$ being equal to or greater than the threshold offset.

In various embodiments of method 600 and/or 700, the one of the first plurality of Z-stack images depicts a fluorescent object. In some instances, when the position offset is less than the threshold offset and the computed standard deviation is less than a threshold standard deviation, the adjusting the position information includes shifting an x-direction position of the fluorescent object by OFF-x and/or a y-direction position of the fluorescent object by OFF-y.

Figure 8:
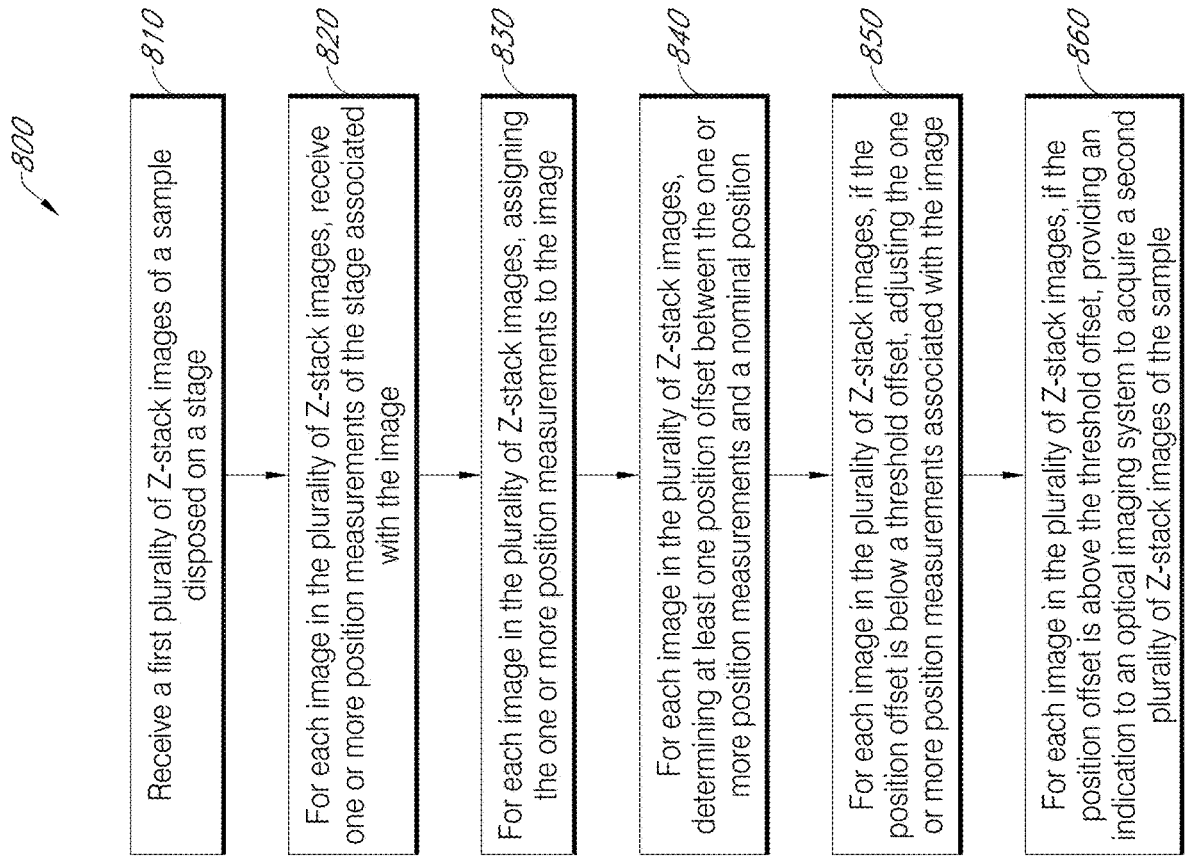
FIG. 8 is a flowchart illustrating an example method for improving the imaging of samples by an opto-fluidic instrument, according to various embodiments.

FIG. 8 is a flowchart illustrating an example method 800 for improving the imaging of samples by an opto-fluidic instrument, according to various embodiments. Aspects of the method 800 can be executed by the optics module 150, the sample module 160, the system controller 130, of FIG. 1, and/or other suitable means for performing the steps. As illustrated, the method 800 includes a number of enumerated steps, but aspects of the method 800 may include additional steps before, after, and in between the enumerated steps. In some embodiments, one or more of the enumerated steps may be omitted or performed in a different order.

At block 810, in various embodiments, a first plurality of Z-stack images of a sample disposed on a stage are received.

At block 820, in various embodiments, for each image in the plurality of Z-stack images, one or more position measurements of the stage associated with the image are received.

At block 830, in various embodiments, for each image in the plurality of Z-stack images, the one or more position measurements to the image are assigned.

At block 840, in various embodiments, for each image in the plurality of Z-stack images, at least one position offset between the one or more position measurements and a nominal position is determined.

At block 850, in various embodiments, for each image in the plurality of Z-stack images, if the position offset is below a threshold offset, the one or more position measurements associated with the image is adjusted.

At block 860, in various embodiments, for each image in the plurality of Z-stack images, if the position offset is above the threshold offset, an indication to an optical imaging system to acquire a second plurality of Z-stack images of the sample is provided.

In some embodiments, one or more aspects of method 800 may be a part of program instructions executable by a processor. For example, in some embodiments, a computer program product may comprise a computer readable storage medium having program instructions embodied therewith. The program instructions may be executable by a processor to cause the processor to perform a method comprising: receiving a first plurality of Z-stack images of a sample disposed on a stage; for each image in the plurality of Z-stack images:

receiving one or more position measurements of the stage associated with the image; assigning the one or more position measurements to the image; determining at least one position offset between the one or more position measurements and a nominal position; and if the position offset is below a threshold offset, adjusting the one or more position measurements associated with the image if the position offset is above the threshold offset, providing an indication to an optical imaging system to acquire a second plurality of Z-stack images of the sample.

In various embodiments, displacement correction of an image may be performed such that offsets are calculated from the difference between the target and measured positions at which image was acquired and the offsets are applied directly to the 2D image array. In various embodiments, only the X and Y offsets are applied to offset the array. Exemplary pseudocode implementing displacement correction is shown below:

```
FOR z_stack_id IN z_stack ids:
    FOR z_index IN RANGE(z_stack_height):
        tx, ty=get_target_position(z_stack_id, z_index)
        mx, my=get_measured_position(z_stack_id, z_index)
        offset_x=convert_motor_to_pixel_units(mx−tx)
        offset_y=convert_motor_to_pixel_units(my−ty)
        image_array=image_arrays[z_stack_id][z_index]
        updated_array=shift_array_with_interpolation(image_array, offset_x, offset_y)
        image_arrays[z_stack_id][z_index]=updated_array
```

In various embodiments, displacement correction of object locations may be performed such that offsets are calculated from the difference between the target and measured positions at which image was acquired and the offsets are applied to object locations derived from the affected image. In various embodiments, X, Y, and Z offsets are applied to the object locations in the affected image. Exemplary pseudocode implementing displacement correction is shown below:

```
FOR z stack id IN z_stack ids:
    FOR z index IN RANGE(z_stack_height):
        tx, ty, tz=get_target_position(z_stack_id, z_index)
        mx, my, mz=get_measured_position(z_stack_id, z_index)
        offset_x=convert_motor_to_pixel_units(mx−tx)
        offset_y=convert_motor_to_pixel_units(my−ty)
        offset_z=convert_motor_to_pixel_units(mz−tz)
        obj_locs_xyz=get_obj_locs_by_xyz(z_stack_id, z_index)
        updated_locs_xyz=shift_obj_locs(obj_locations_xyz, offset_x, offset_y, offset_z)
        save_obj_locs_by_xyz(updated_locs_xyz, z_stack_id, z_index)
```

Figure 9:
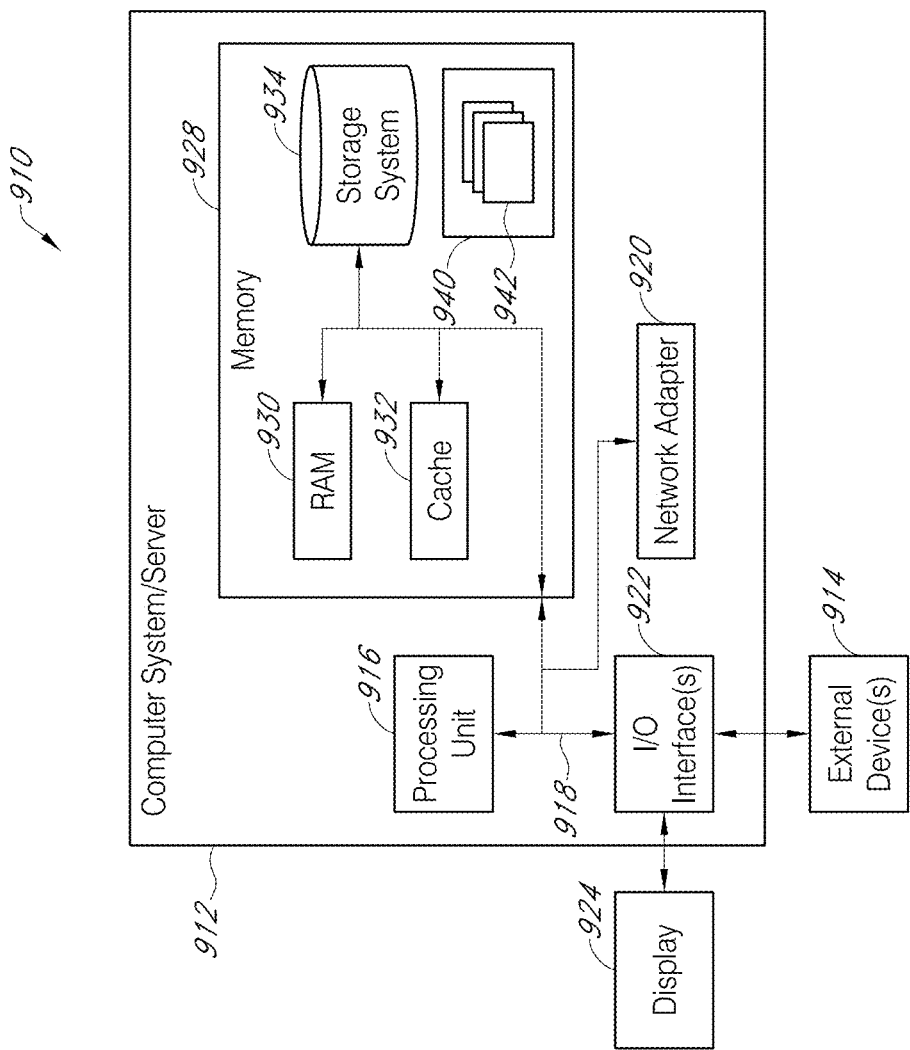
FIG. 9 illustrates a block diagram of a computing node, according to various embodiments.

Referring now to FIG. 9, a schematic of an example of a computing node is shown. Computing node 910 is only one example of a suitable computing node and is not intended to suggest any limitation as to the scope of use or functionality of embodiments of the disclosure described herein. Regardless, computing node 910 is capable of being implemented and/or performing any of the functionality set forth hereinabove.

In computing node 910 there is a computer system/server 912, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 912 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 912 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 912 in computing node 910 is shown in the form of a general-purpose computing device. The components of computer system/server 912 may include, but are not limited to, one or more processors or processing units 916, a system memory 928, and a bus 918 that couples various system components including system memory 928 to processor 916.

Bus 918 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 912 typically includes a variety of computer system readable media. Such media may be any available media that is accessible by computer system/server 912, and it includes both volatile and non-volatile media, removable and non-removable media.

System memory 928 can include computer system readable media in the form of volatile memory, such as random access memory (RAM) 930 and/or cache memory 932. Computer system/server 912 may further include other removable/non-removable, volatile/non-volatile computer system storage media. By way of example only, storage system 934 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 918 by one or more data media interfaces. As will be further depicted and described below, memory 928 may include at least one program product having a set (e.g., at least one) of program modules that are configured to carry out the functions of embodiments of the disclosure.

Program/utility 940, having a set (at least one) of program modules 942, may be stored in memory 928 by way of example, and not limitation, as well as an operating system, one or more application programs, other program modules, and program data. Each of the operating system, one or more application programs, other program modules, and program data or some combination thereof, may include an implementation of a networking environment. Program modules 942 generally carry out the functions and/or methodologies of embodiments of the disclosure as described herein.

Computer system/server 912 may also communicate with one or more external devices 914 such as a keyboard, a pointing device, a display 924, etc.; one or more devices that enable a user to interact with computer system/server 912; and/or any devices (e.g., network card, modem, etc.) that enable computer system/server 912 to communicate with one or more other computing devices. Such communication can occur via Input/Output (I/O) interfaces 922. Still yet, computer system/server 912 can communicate with one or more networks such as a local area network (LAN), a general wide area network (WAN), and/or a public network (e.g., the Internet) via network adapter 920. As depicted, network adapter 920 communicates with the other components of computer system/server 912 via bus 918. It should be understood that although not shown, other hardware and/or software components could be used in conjunction with computer system/server 912. Examples, include, but are not limited to: microcode, device drivers, redundant processing units, external disk drive arrays, RAID systems, tape drives, and data archival storage systems, etc.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the present teachings are described in conjunction with various embodiments, it is not intended that the present teachings be limited to such various embodiments. On the contrary, the present teachings encompass various alternatives, modifications, and equivalents, as will be appreciated by those of skill in the art.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

VI. Recitation of Embodiments

Embodiment 1: A method, comprising: acquiring, using an optical imaging system, a first plurality of Z-stack images of a sample supported by an XY-stage, wherein the first plurality of Z-stack images are images of a respective plurality of two-dimensional (2D) slices of the sample; measuring, using a position sensor coupled to the XY-stage, a position of one of the plurality of 2D slices, wherein one of the first plurality of Z-stack images is an image of the one of the plurality of 2D slices; computing, using a processor coupled to the position sensor, a position offset between the measured position and a nominal position, of the one of the plurality of 2D slices; and determining whether to adjust, using the processor, the position information associated with the one of the first plurality of Z-stack images, or acquire, using the optical imaging system, a second plurality of Z-stack images of the sample, based at least in part on a comparison of the position offset and a threshold offset.

Embodiment 2: The method of embodiment 1, wherein the optical imaging system includes an epifluorescence microscope.

Embodiment 3: The method of embodiment 1 or 2, wherein the acquiring the first plurality of Z-stack images includes moving the sample in X-direction or Y-direction using the XY-stage during the acquiring of the first plurality of Z-stack images by the optical imaging system.

Embodiment 4: The method of any of the preceding embodiments, wherein the acquiring the first plurality of Z-stack images occurs at a rate ranging from about 10 Hz to about 20 Hz.

Embodiment 5: The method of any of the preceding embodiments, wherein the measuring the position of one of the plurality of 2D slices occurs at a rate ranging from about 500 Hz to about 10 kHz.

Embodiment 6: The method of any of the preceding embodiments, wherein successive 2D slices of the plurality of 2D slices are separated from each other by a distance ranging from about 500 nm to about 1000 nm.

Embodiment 7: The method of any of the preceding embodiments, wherein the position sensor is an optical encoder.

Embodiment 8: The method of any of embodiments 1-6, wherein the position sensor is a potentiometric position sensor, a capacitive position sensor, a fiber-optic position sensor, or an ultrasonic position sensor.

Embodiment 9: The method of any of the preceding embodiments, wherein the optical imaging system is coupled to a Z-stage configured to move an objective lens of the optical imaging system in the Z-direction.

Embodiment 10: The method of embodiment 9, wherein the acquiring the first plurality of Z-stack images includes moving, using the Z-stage, the objective lens of the optical imaging system in the Z-direction during the acquiring of the first plurality of Z-stack images by the optical imaging system.

Embodiment 11: The method of embodiment 9 or 10, wherein: the position of one of the plurality of 2D slices includes an X-Y position of the one of the plurality of 2D slices; and the position sensor is coupled to the XY-stage and is configured to measure the X-Y position of the one of the plurality of 2D slices.

Embodiment 12: The method of any of the preceding embodiments, wherein the plurality of 2D slices correspond to focal planes of an objective lens of the optical imaging system.

Embodiment 13: The method of any of the preceding embodiments, wherein the determining includes determining to adjust the position information when the position offset is less than a threshold offset.

Embodiment 14: The method of any of embodiments 1-12, wherein the determining includes determining to acquire the second plurality of Z-stack images when the position offset is equal to or greater than the threshold offset.

Embodiment 15: The method of any of embodiments 1-12, wherein the position of the one of the plurality of 2D slices includes a plurality of positions of the one of the plurality of 2D slices and the position offset includes a plurality of position offsets between the plurality of positions and the nominal position of the one of the plurality of 2D slices, the method further comprising: computing, using the processor, a standard deviation of the plurality of positions offsets.

Embodiment 16: The method of embodiment 15, wherein the determining includes determining to adjust the position information when the computed standard deviation is less than a threshold standard deviation and the position offset is less than a threshold offset.

Embodiment 17: The method of embodiment 15, wherein the determining includes determining to acquire the second plurality of Z-stack images when the computed standard deviation is equal to or greater than a threshold standard deviation and/or the position offset is equal to or greater than a threshold offset.

Embodiment 18: The method of embodiment 16, wherein: the measured position includes an x-direction measured position value ("MPV-x"), and a y-direction measured position value ("MPV-y"), and the nominal position includes an x-direction nominal position value ("NPV-x"), and a y-direction nominal position value ("NPV-y"); the position offset includes an x-direction offset ("OFF-x") between MPV-x and NPV-x, and a y-direction offset ("OFF-y") between MPV-y and NPV-y; the threshold offset includes an x-direction threshold offset ("TO-x") and a y-direction threshold offset ("TO-y"); and the position offset being less than the threshold offset includes the OFF-x and the OFF-y being less than the TO-x and the TO-y, respectively.

Embodiment 19: The method of embodiment 17, wherein: the measured position includes an x-direction measured position value ("MPV-x"), and a y-direction measured position value ("MPV-y"), and the nominal position includes an x-direction nominal position value ("NPV-x"), and a y-direction nominal position value ("NPV-y"); the position offset includes an x-direction offset ("OFF-x") between MPV-x and NPV-x, and a y-direction offset ("OFF-y") between MPV-y and NPV-y; the threshold offset includes an x-direction threshold offset ("TO-x") and a y-direction threshold offset ("TO-y"); and the position offset being equal to or greater than the threshold offset includes the OFF-x and the OFF-y, or a z-direction offset ("OFF-z") being equal to or greater than the TO-x, the TO-y, or a z-direction threshold offset ("TO-z"), respectively.

Embodiment 20: The method of embodiment 16, wherein: the measured position includes an x-direction measured position value ("MPV-x") and a y-direction measured position value ("MPV-y"), and the nominal position includes an x-direction nominal position value ("NPV-x") and a y-direction nominal position value ("NPV-y"); the position offset includes an x-direction offset ("OFF-x") between MPV-x and NPV-x and a y-direction offset ("OFF-y") between MPV-y and NPV-y; and the position offset being less than or greater than the threshold offset includes $((OFF\text{-}x)^2+(OFF\text{-}y)^2)^{0.5}$ being less than the threshold offset.

Embodiment 21: The method of embodiment 17, wherein: the measured position includes an x-direction measured position value ("MPV-x") and a y-direction measured position value ("MPV-y"), and the nominal position includes an x-direction nominal position value ("NPV-x") and a y-direction nominal position value ("NPV-y"); the position offset includes an x-direction offset ("OFF-x") between MPV-x and NPV-x and a y-direction offset ("OFF-y") between MPV-y and NPV-y; and the position offset being less than or greater than the threshold offset includes $((OFF\text{-}x)^2+(OFF\text{-}y)^2)^{0.5}$ being equal to or greater than the threshold offset.

Embodiment 22: The method of embodiment 16, 18 or 20, wherein: the measured position includes an x-direction measured position value ("MPV-x") and a y-direction measured position value ("MPV-y"), and the nominal position includes an x-direction nominal position value ("NPV-x") and a y-direction nominal position value ("NPV-y"); the position offset includes an x-direction offset ("OFF-x") between MPV-x and NPV-x and a y-direction offset ("OFF-y") between MPV-y and NPV-y; the one of the first plurality of Z-stack images depicts a fluorescent object; and the adjusting the position information includes shifting an x-direction position of the fluorescent object by the OFF-x and/or a y-direction position of the fluorescent object by the OFF-y.

Embodiment 23: A system, comprising: an XY-stage configured to support a sample; an optical imaging system configured to acquire a first plurality of Z-stack images of a sample supported by an XY-stage, wherein the first plurality of Z-stack images are images of a respective plurality of two-dimensional (2D) slices of the sample; a position sensor coupled to the XY-stage and configured to measure a position of one of the plurality of 2D slices, wherein one of the first plurality of Z-stack images is an image of the one of the plurality of 2D slices; and a processor coupled to the position sensor and configured to: compute a position offset between the measured position and a nominal position, of the one of the plurality of 2D slices; and determine whether to adjust, using the processor, position information associated with the one of the first plurality of Z-stack images, or acquire, using the optical imaging system, a second plurality of Z-stack images of the sample based at least in part on a comparison of the position offset with a threshold offset.

Embodiment 24: The system of embodiment 23, wherein the optical imaging system includes an epifluorescence microscope.

Embodiment 25: The system of embodiment 23 or 24, wherein the position sensor is an optical encoder.

Embodiment 26: The system of any of embodiments 23-25, further comprising a Z-stage coupled to the optical imaging system and configured to move an objective lens of the optical imaging system in the Z-direction.

Embodiment 27: The system of any of embodiments 23-26, wherein: the position of one of the plurality of 2D slices includes an X-Y position of the one of the plurality of 2D slices; and the position sensor is coupled to the XY-stage and is configured to measure the X-Y position of the one of the plurality of 2D slices.

Embodiment 28: The system of any of embodiments 23-27, wherein the position of the one of the plurality of 2D slices includes a plurality of positions of the one of the plurality of 2D slices and the position offset includes a plurality of position offsets between the plurality of positions and the nominal position of the one of the plurality of 2D slices, the processor further configured to: compute a standard deviation of the plurality of position offsets.

Embodiment 29: The system of embodiment 28, wherein the processor determines to adjust the position information when the computed standard deviation is less than a threshold standard deviation and the position offset is less than a threshold offset.

Embodiment 30: The system of embodiment 28, wherein the processor determines to acquire the second plurality of Z-stack images when the computed standard deviation is equal to or greater than a threshold standard deviation and/or the position offset is equal to or greater than a threshold offset.

Embodiment 31: The system of embodiment 16, 18 or 20, wherein: the measured position includes an x-direction measured position value ("MPV-x") and a y-direction measured position value ("MPV-y"), and the nominal position includes an x-direction nominal position value ("NPV-x") and a y-direction nominal position value ("NPV-y"); the position offset includes an x-direction offset ("OFF-x") between MPV-x and NPV-x and a y-direction offset ("OFF-y") between MPV-y and NPV-y; the one of the first plurality of Z-stack images depicts a fluorescent object; and the processor adjusts the position information by shifting an x-direction position of the fluorescent object by the OFF-x and/or a y-direction position of the fluorescent object by the OFF-y.

Embodiment 32: A method, comprising: receiving a first plurality of Z-stack images of a sample disposed on a stage; for each image in the plurality of Z-stack images: receiving one or more position measurements of the stage associated with the image; assigning the one or more position measurements to the image; determining at least one position offset between the one or more position measurements and a nominal position; and if the position offset is below a threshold offset, adjusting the one or more position measurements associated with the image if the position offset is above the threshold offset, providing an indication to an optical imaging system to acquire a second plurality of Z-stack images of the sample.

Embodiment 33: A computer program product comprising a computer readable storage medium having program instructions embodied therewith, the program instructions executable by a processor to cause the processor to perform a method comprising: receiving a first plurality of Z-stack images of a sample disposed on a stage; for each image in the plurality of Z-stack images: receiving one or more position measurements of the stage associated with the image; assigning the one or more position measurements to the image; determining at least one position offset between the one or more position measurements and a nominal position; and if the position offset is below a threshold offset, adjusting the one or more position measurements associated with the image if the position offset is above the threshold offset, providing an indication to an optical imaging system to acquire a second plurality of Z-stack images of the sample.

Embodiment 34: A system, comprising: a computing node comprising a computer readable storage medium having program instructions embodied therewith, the program instructions executable by a processor to cause the processor to perform a method comprising: receiving a first plurality of Z-stack images of a sample disposed on a stage; for each image in the plurality of Z-stack images: receiving one or more position measurements of the stage associated with the image; assigning the one or more position measurements to the image; determining at least one position offset between the one or more position measurements and a nominal position; and if the position offset is below a threshold offset, adjusting the one or more position measurements associated with the image if the position offset is above the threshold offset, providing an indication to an optical imaging system to acquire a second plurality of Z-stack images of the sample.

What is claimed is:

1. A method, comprising:
    acquiring, using an optical imaging system, a first plurality of Z-stack images of a sample supported by an XY-stage, wherein the first plurality of Z-stack images are images of a respective plurality of two-dimensional (2D) slices of the sample;
    measuring, using a position sensor coupled to the XY-stage, a position of one of the plurality of 2D slices, wherein one of the first plurality of Z-stack images is an image of the one of the plurality of 2D slices;
    computing, using a processor coupled to the position sensor, a position offset between the measured position and a nominal position, of the one of the plurality of 2D slices; and
    determining whether to adjust, using the processor, the position information associated with the one of the first plurality of Z-stack images, or acquire, using the optical imaging system, a second plurality of Z-stack images of the sample, based at least in part on a comparison of the position offset and a threshold offset.

2. The method of claim 1, wherein the optical imaging system includes an epifluorescence microscope.

3. The method of claim 1, wherein the acquiring the first plurality of Z-stack images includes moving the sample in X-direction or Y-direction using the XY-stage during the acquiring of the first plurality of Z-stack images by the optical imaging system.

4. The method of claim 1, wherein the acquiring the first plurality of Z-stack images occurs at a rate ranging from about 10 Hz to about 20 Hz.

5. The method of claim 1, wherein the measuring the position of one of the plurality of 2D slices occurs at a rate ranging from about 500 Hz to about 10 kHz.

6. The method of claim 1, wherein successive 2D slices of the plurality of 2D slices are separated from each other by a distance ranging from about 500 nm to about 1000 nm.

7. The method of claim 1, wherein the optical imaging system is coupled to a Z-stage configured to move an objective lens of the optical imaging system in the Z-direction.

8. The method of claim 7, wherein the acquiring the first plurality of Z-stack images includes moving, using the Z-stage, the objective lens of the optical imaging system in the Z-direction during the acquiring of the first plurality of Z-stack images by the optical imaging system.

9. The method of claim 7, wherein:
    the position of one of the plurality of 2D slices includes an X-Y position of the one of the plurality of 2D slices; and
    the position sensor is coupled to the XY-stage and is configured to measure the X-Y position of the one of the plurality of 2D slices.

10. The method of claim 1, wherein the plurality of 2D slices correspond to focal planes of an objective lens of the optical imaging system.

11. The method of claim 1, wherein the determining includes determining to adjust the position information when the position offset is less than a threshold offset.

12. The method of claim 1, wherein the determining includes determining to acquire the second plurality of Z-stack images when the position offset is equal to or greater than the threshold offset.

13. The method of claim 1, wherein the position of the one of the plurality of 2D slices includes a plurality of positions of the one of the plurality of 2D slices and the position offset includes a plurality of position offsets between the plurality of positions and the nominal position of the one of the plurality of 2D slices, the method further comprising:
    computing, using the processor, a standard deviation of the plurality of positions offsets.

14. The method of claim 13, wherein the determining includes determining to adjust the position information when the computed standard deviation is less than a threshold standard deviation and the position offset is less than a threshold offset.

15. The method of claim 14, wherein:
    the measured position includes an x-direction measured position value ("MPV-x"), and a y-direction measured position value ("MPV-y"), and the nominal position includes an x-direction nominal position value ("NPV-x"), and a y-direction nominal position value ("NPV-y");
    the position offset includes an x-direction offset ("OFF-x") between MPV-x and NPV-x, and a y-direction offset ("OFF-y") between MPV-y and NPV-y;
    the threshold offset includes an x-direction threshold offset ("TO-x") and a y-direction threshold offset ("TO-y"); and
    the position offset being less than the threshold offset includes the OFF-x and the OFF-y being less than the TO-x and the TO-y, respectively.

16. The method of claim 14, wherein:
    the measured position includes an x-direction measured position value ("MPV-x") and a y-direction measured position value ("MPV-y"), and the nominal position includes an x-direction nominal position value ("NPV-x") and a y-direction nominal position value ("NPV-y");
    the position offset includes an x-direction offset ("OFF-x") between MPV-x and NPV-x and a y-direction offset ("OFF-y") between MPV-y and NPV-y; and
    the position offset being less than or greater than the threshold offset includes $((OFF\text{-}x)^2+(OFF\text{-}y)^2)^{0.5}$ being less than the threshold offset.

17. The method of claim 14, wherein:
    the measured position includes an x-direction measured position value ("MPV-x") and a y-direction measured position value ("MPV-y"), and the nominal position includes an x-direction nominal position value ("NPV-x") and a y-direction nominal position value ("NPV-y");
    the position offset includes an x-direction offset ("OFF-x") between MPV-x and NPV-x and a y-direction offset ("OFF-y") between MPV-y and NPV-y;
    the one of the first plurality of Z-stack images depicts a fluorescent object; and
    the adjusting the position information includes shifting an x-direction position of the fluorescent object by the OFF-x and/or a y-direction position of the fluorescent object by the OFF-y.

18. The method of claim 13, wherein the determining includes determining to acquire the second plurality of Z-stack images when the computed standard deviation is equal to or greater than a threshold standard deviation and/or the position offset is equal to or greater than a threshold offset.

19. The method of claim 18, wherein:
    the measured position includes an x-direction measured position value ("MPV-x"), and a y-direction measured position value ("MPV-y"), and the nominal position includes an x-direction nominal position value ("NPV-x"), and a y-direction nominal position value ("NPV-y");

the position offset includes an x-direction offset ("OFF-x") between MPV-x and NPV-x, and a y-direction offset ("OFF-y") between MPV-y and NPV-y;

the threshold offset includes an x-direction threshold offset ("TO-x") and a y-direction threshold offset ("TO-y"); and the position offset being equal to or greater than the threshold offset includes the OFF-x and the OFF-y, or a z-direction offset ("OFF-z") being equal to or greater than the TO-x, the TO-y, or a z-direction threshold offset ("TO-z"), respectively.

20. The method of claim 18, wherein:

the measured position includes an x-direction measured position value ("MPV-x") and a y-direction measured position value ("MPV-y"), and the nominal position includes an x-direction nominal position value ("NPV-x") and a y-direction nominal position value ("NPV-y");

the position offset includes an x-direction offset ("OFF-x") between MPV-x and NPV-x and a y-direction offset ("OFF-y") between MPV-y and NPV-y; and the position offset being less than or greater than the threshold offset includes $((\text{OFF-x})^2+(\text{OFF-y})^2)^{0.5}$ being equal to or greater than the threshold offset.

* * * * *